United States Patent
Beaudoin

(10) Patent No.: US 11,890,350 B2
(45) Date of Patent: Feb. 6, 2024

(54) STEROID ACID-PEPTIDE BASED CYTOTOXIC COMPOUNDS

(71) Applicant: DEFENCE THERAPEUTICS INC., Vancouver (CA)

(72) Inventor: Simon Beaudoin, Sherbrooke (CA)

(73) Assignee: DEFENCE THERAPEUTICS INC., Vancouver (CA)

( * ) Notice: Subject to any disclaimer, the term of this patent is extended or adjusted under 35 U.S.C. 154(b) by 0 days.

(21) Appl. No.: 18/056,110

(22) Filed: Nov. 16, 2022

(65) Prior Publication Data

US 2023/0226210 A1 Jul. 20, 2023

Related U.S. Application Data

(60) Provisional application No. 63/264,126, filed on Nov. 16, 2021.

(51) Int. Cl.
| | |
|---|---|
| *A61K 47/68* | (2017.01) |
| *A61K 47/55* | (2017.01) |
| *A61K 47/64* | (2017.01) |
| *A61P 35/00* | (2006.01) |
| *A61K 45/06* | (2006.01) |

(52) U.S. Cl.
CPC .......... *A61K 47/6811* (2017.08); *A61K 45/06* (2013.01); *A61K 47/55* (2017.08); *A61K 47/64* (2017.08); *A61K 47/6803* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 5,955,365 A | 9/1999 | Szoka, Jr. et al. | |
| 7,732,177 B2 | 6/2010 | Iadonato et al. | |
| 11,291,717 B1 | 4/2022 | Beaudoin | |
| 11,612,651 B2 * | 3/2023 | Beaudoin | A61K 47/64 424/185.1 |

FOREIGN PATENT DOCUMENTS

| | | |
|---|---|---|
| CN | 101049505 A | 10/2007 |
| EP | 1046394 A2 | 10/2000 |
| WO | 2017/156630 A1 | 9/2017 |
| WO | 2018/165752 A1 | 9/2018 |
| WO | 2020/252298 A1 | 12/2020 |
| WO | 2022/126239 A1 | 6/2022 |
| WO | 2022/232945 A1 | 11/2022 |

OTHER PUBLICATIONS

Al-Hilal et al., "Functional transformations of bile acid transporters induced by high-affinity macromolecules," *Scientific Reports* 4:4163, Feb. 2014. (10 pages).
Anding et al., "Cleaning House: Selective Autophagy of Organelles," *Developmental Cell* 41:10-22, Apr. 2017. (13 pages).
Anguille et al., "Clinical use of dendritic cells for cancer therapy," *The Lancet Oncology* 15:e257-e267, Jun. 2014. (11 pages).
Chang et al., "Bile acids are essential for porcine enteric calicivirus replication in association with down-regulation of signal transducer and activator of transcription 1," *PNAS* 101(23):8733-8738, Jun. 2004. (6 pages).
Chugh et al., "Cell-Penetrating Peptides: Nanocarrier for Macromolecule Delivery in Living Cells," *IUBMB Life* 62(3):183-193, Mar. 2010. (11 pages).
Kenney et al., "Identification and Fine Mapping of Nuclear and Nucleolar Localization Signals within the Human Ribosomal Protein S17," *Plos One* 10(4):e0124396, Apr. 2015. (17 pages).
Kim et al.,"Homodimeric SV40 NLS peptide formed by disulfide bond as enhancer for gene delivery," *Bioorganic & Medicinal Chemistry Letters* 22:5415-5418, Jul. 2012. (4 pages).
Kim et al., "The molecular mechanism for nuclear transport and its application," *Anatomy & Cell Biology* 50: 77-85, Jun. 2017. (9 pages).
Kosugi et al., "Six Classes of Nuclear Localization Signals Specific to Different Binding Grooves of Importin α" *Journal of Biological Chemistry* 284(1):478-485, Jan. 2009. (8 pages).
Lam et al., "Progress and prospects: nuclear import of nonviral vectors," *Gene Therapy* 17(4):439-447, Apr. 2010 (NIH Public Access Author Manuscript, available in PMC Jul. 7, 2014) (17 pages).
Leyton et al., "Auger Electron Radioimmunotherapeutic Agent Specific for the CD123+/CD131− Phenotype of the Leukemia Stem Cell Population," *The Journal of Nuclear Medicine* 52(9):1465-1473, Sep. 2011. (9 pages).
Linke et al., "Stimulation of Acid Sphingomyelinase Activity by Lysosomal Lipids and Sphingolipid Activator Proteins," Biological Chemistry 382:283-290, Feb. 2001. (8 pages).
Liu et al., "The Renpenning syndrome-associated protein PQBP1 facilitates the nuclear import of splicing factor TXNL4A through the karyopherin β2 receptor," *Journal of Biological Chemistry* 295(13):4093-4100, Feb. 2020. (8 pages).
Lu et al., "Types of nuclear localization signals and mechanisms of protein import into the nucleus," *Cell Communication and Signaling* 19:60, May 2021. (10 pages).

(Continued)

*Primary Examiner* — Ruixiang Li
(74) *Attorney, Agent, or Firm* — Seed IP Law Group LLP

(57) ABSTRACT

Agents having cytotoxic activity, as well as compositions, uses, and methods relating thereto, are described herein. Certain steroid acid-peptide conjugates or moieties have the ability to induce killing or inhibition of proliferation of mammalian cells, in vitro or in vivo upon administration to a subject. The steroid acid-peptide conjugates include bile acids and bile acid analogs and peptides that may include a nuclear localisation signal or a portion thereof. Also described herein is a method for treating cancer, an autoimmune disease, or any other disease or disorder ameliorated by treatment with an antiproliferative drug in a subject in a subject with the cytotoxic agents described herein.

20 Claims, 12 Drawing Sheets

Specification includes a Sequence Listing.

(56) References Cited

OTHER PUBLICATIONS

Manoharan et al., "Cholic Acid-Oligonucleotide Conjugates for Antisense Applications," *Bioorganic & Medicinal Chemistry Letters* 4(8):1053-1060, Apr. 1994. (8 pages).

Ogris et al., "Melittin Enables Efficient Vesicular Escape and Enhanced Nuclear Access of Nonviral Gene Delivery Vectors," *Journal of Biological Chemistry* 276(50):47550-47555, Dec. 2001. (6 pages).

Patel et al., "Next generation approaches for tumor vaccination," *Chinese Clinical Oncology* 6(2):19, Feb. 2017. (12 pages).

Raouane et al., "Lipid Conjugated Oligonucleotides: A Useful Strategy for Delivery," *Bioconjugate Chemistry* 23:1091-1104, Feb. 2012. (15 pages).

Ray et al.,"Quantitative tracking of protein trafficking to the nucleus using cytosolic protein delivery by nanoparticle-stabilized nanocapsules," *Bioconjugate Chemistry* 26(6): 1004-1007, Jun. 2015. (HHS Public Access Author Manuscript, available in PMC Jun. 17, 2016) (6 pages).

Smith et al., "Alternative tumour-specific antigens," *Nature Reviews* 19:465-478, Aug. 2019 (available online Jul. 2019) (14 pages).

Tagliamonte et al., "Antigen-specific vaccines for cancer treatment," *Human Vaccines & Immunotherapeutics* 10(11):3332-3346, Nov. 2014. (15 pages).

Tomatsidou, "Evaluation of peptide-mediated nucleic acid delivery," Drug Innovation Masters—Thesis, Department of Pharmaceutics, Utrecht Institute of Pharmaceutical Sciences (UIPS), Utrecht University, Nov. 2012-Feb. 2013. (33 pages).

Wang et al., "HMGB1 in inflammation and cancer," *Journal of Hematology & Oncology* 13:116, Aug. 2020. (4 pages).

Azuar et al., "Cholic Acid-based Delivery System for Vaccine Candidates against Group A *Streptococcus*," *ACS Medicinal Chemistry Letters*, 10: 1253-1529 (2019).

Beaudoin et al., "ChAcNLS, a novel modification to antibody-conjugates permitting target cell-specific endosomal escape, localization to the nucleus and enhanced total intracellular accumulation," *Molecular Pharmaceutics*, 13(6): 1915-26 (2016).

Beaudoin et al., "Initial Evaluation of Antibody-conjugates Modified with Viral-derived Peptides for Increasing Cellular Accumulation and Improving Tumor Targeting," *Journal of Visualized Experiments* 133: 55440 (2018).

Beck et al., "Strategies and challenges for the next generation of antibody-drug conjugates.," *Nature Reviews Drug Discovery*, 16: 315-337 (2017).

El-Kadiry et al., "Accum™ Technology: A Novel Conjugable Primer for Onco-Immunotherapy," Molecules, 27(12): 3807 (2022).

Hanafi et al., "Overview of Bile Acids Signaling and Perspective on the Signal of Ursodeoxycholic Acid, the Most Hydrophilic Bile Acid, in the Heart," *Biomolecules* 84(4):159 (2018).

Murakami et al., "Bile acids and ceramide overcome the entry restriction for GII.3 human norovirus replication in human intestinal enteroids," *Proceedings of the National Academy of Sciences USA* 117(3):1700-1710 (2020).

Paquette et al., "NLS-Cholic Acid Conjugation to IL-5Ra-Specific Antibody Improves Cellular Accumulation and In Vivo Tumor-Targeting Properties in a Bladder Cancer Model," *Bioconjugate Chemistry*. 29: 1352-1363 (2018).

Shivanna et al., "The crucial role of bile acids in the entry of porcine enteric calicivirus," *Virology* 456-457: 268-278 (2014).

Shivanna et al., "Ceramide formation mediated by acid sphingomyelinase facilitates endosomal escape of caliciviruses," *Virology*, 483, 218-228 (2015).

Sun et al., "Factors influencing the nuclear targeting ability of nuclear localization signals," *Journal of Drug Targeting*, 24(10): 927-933 (2016).

Swaan et al., "Enhanced Transepithelial Transport of Peptides by Conjugation to Cholic Acid," *Bioconjugate Chemistry* 8(4): 520-525 (1997).

U.S. Appl. No. 17/709,599, "Covalently Modified Antigens for Improved Immune Response and/or Stability," 78 pages, filed Mar. 31, 2022.

Beaudoin et al., "Antibodies with integrated endosome escape and multi-directional escape and multi-direction intracellular trafficking-control capabilities for molecular transport and accumulation of a BODIPY-based dye," *J Nucl Med* 57(supplement 2): 1215, Abstract, 2 pages (2016).

De Loos et al., "Design and Application of Self-Assembled Low Molecular Weight Hydrogels," *Eur. J. Org. Chem.* 3615-3631 (2005).

International Search Report for International Application No. PCT/CA2022/051692, 8 pages, dated Feb. 15, 2023.

Lacasse et al., "A Novel Proteomic Method Reveals NLS Tagging of T-DM1 Contravenes Classical Nuclear Transport in a Model of HER2-Positive Breast Cancer," *Molecular Therapy: Methods & Clinical Development* 19:99-119 (2020).

Paquette et al., "ChAcNLS-A14, a novel antibody-conjugate PET tracer for targeting human IL-5Rα-positive muscle invasive bladder cancer," *J Nucl Med* 57 (Supplement 2 52), Abstract, 2 pages, (2016).

Sangeetha et al., "Properties of Hydrogels Derived from Cationic Analogues of Bile Acid: Remarkably Distinct Flowing Characteristics," *J. Phys. Chem. B* 108:16056-16063 (2004).

Pavlović et al., "Bile Acids and Their Derivatives as Potential Modifiers of Drug Release and Pharmacokinetic Profiles," *Frontiers in Pharmacology 9*, Article 1283, 23 pages (Nov. 2018).

Raucher et al., "Cell-penetrating peptides: strategies for anticancer treatment," *Trends in Molecular Medicine* 21(9):560-70 (Sep. 2015).

* cited by examiner

STEROID ACID-PEPTIDE BASED CYTOTOXIC COMPOUNDS

The present description relates to steroid acid-peptide based cytotoxic compounds. More specifically, the present description relates to steroid acid-peptide conjugates as cytotoxic compounds and use thereof for the treatment of diseases and disorders.

BACKGROUND

Despite recent advances in treatments of cancers and autoimmune diseases, chemotherapeutic and immunosuppressive drugs remain among the most effective approaches for management of these diseases. Cytotoxic compounds in particular have applications as anti-proliferative and immunosuppressive drugs, yet their non-specific nature, severe associated side effects, and the development of resistance against conventional drugs has created an urgent need to develop new classes of cytotoxic agents. While antibody-drug conjugates (ADCs), in which cytotoxic compounds are conjugated to monoclonal antibodies, have been developed as more targeted therapies, the inherent toxicity of the compounds remain, leading to harsh side effects. In this regard, a stable linkage between the antibody and cytotoxic compound has been generally considered a crucial aspect of conventional ADCs to ensure that the cytotoxic payload does not detach from the antibody before reaching its target cell (Beck et al., 2017). Recently, intracellular accumulation of ADCs in their target cells has been shown to be enhanced by covalently modifying the antibody with a cholic acid-NLS peptide moiety, which is thought to facilitate endosomal escape and direct the ADC to the nucleus (Beaudoin et al., 2016; Paquette et al., 2018). Despite these advances, there remains a need for the discovery of novel cytotoxic compounds, that are safer, hydrophilic, effective, and easy to produce.

SUMMARY

In a first aspect, described herein is a pharmaceutical composition comprising a steroid acid-peptide conjugate having cytotoxic or cytostatic activity, the conjugate being free or releasably bound to a carrier molecule.

In another aspect, described herein is a method for treating cancer or any other disease or disorder ameliorated by treatment with an antiproliferative drug in a subject, the method comprising administering a cytotoxic or cytostatic dose of the pharmaceutical composition or steroid acid-peptide conjugate as defined herein, to the subject.

In another aspect, described herein is a method for treating an autoimmune disease in a subject, the method comprising administering a cytotoxic or cytostatic dose of the pharmaceutical composition or steroid acid-peptide conjugate as defined herein, to the subject.

In another aspect, described herein is a use the pharmaceutical composition or steroid acid-peptide conjugate as defined herein, for treating cancer, an autoimmune disease, or any other antiproliferative disease or disorder in a subject; or as a cytotoxic or cytostatic agent.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one," but it is also consistent with the meaning of "one or more", "at least one", and "one or more than one".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the expression "consisting essentially of" or "consists essentially of" refers to those elements required for a given embodiment. The expression permits the presence of additional elements that do not materially affect the basic and novel or functional characteristic(s) of that embodiment of the invention, so long as the additional elements do not decrease the performance (e.g., safety profile or efficacy) of that of the corresponding embodiment "consisting of" the recited elements. For greater clarity, the expressions do not exclude the possibility that other additional non-essential ingredients (e.g., excipients, fillers, stabilizers, or inert components) that do not materially change the function or ability of the steroid acid-peptide moieties to act as cytotoxic or cytostatic agents.

The tem "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1A shows a representative flow cytometry assessment of apoptosis on EL4 lymphoma, CT-26 colon carcinoma, B16 melanoma, and 4T1 breast cancer cells after treatment with the CA-SV40 conjugate (cholic acid-SV40 NLS conjugate) (190 μM). FIG. 1B shows a kill curve showing the $IC_{50}$ of CA-SV40 on EL4 lymphoma cells. CA (Cholic acid) and SV40 NLS alone did not exhibit any cytotoxic activity at the concentrations tested. FIG. 1C shows a representative flow cytometry assessment of apoptosis on mesenchymal stem cells, macrophages, and bone-marrow derived dendritic cells after treatment with the CA-SV40 conjugate (190 μM).

FIG. 2A shows a representative flow cytometry assessment of apoptosis on EL4 lymphoma using both PI (for necrosis) and Annexin-V (for apoptosis). Percentages of double-positive stained cells is shown, which represents late apoptotic cells. FIG. 2B shows representative flow cytometry assessment of Mito-SOX™ staining to detect ROS production at T=0 (grey), T=1 h, T=4 h and T=8 h. FIG. 2C shows the evaluation CA-SV40-induced apoptosis in the presence of N-acetyl-cysteine (NAC) and MitoTempo™ using both $IC_{50}$ and $IC_{100}$ doses.

FIG. 3A shows a schematic representation of the study design with Cytochrome C. FIG. 3B shows a representative flow cytometry assessment of EL4 cell death when treated with CA-SV40 (47 µM) admixed with Cytochrome C.

FIG. 4A shows a schematic diagram of the in vivo experiment design in mice. FIG. 4B shows the tumor growth in response to CA-SV40 using three different doses (blue [47 µM], green [95 µM], and red [190 µM]). FIG. 4C shows Kaplan-Meier survival curves of the experiment shown in FIG. 4B. FIG. 4D shows a schematic diagram of the in vivo experiment design with immune-checkpoint inhibitors in mice. FIG. 4E shows the tumor growth assessment of CA-SV40 alone (red) in comparison to a combination with anti-PD-1 (green) or anti-CTLA4 (blue). EL4 tumors without any treatment (i.e., PBS) are shown in black, whereas anti-PD-1 treatment alone is in orange and anti-CTLA-4 treatment alone is in purple. FIG. 4F shows Kaplan-Meier survival curves of the experiment displayed in FIG. 4E.

FIG. 7A shows the tumor growth in response to CA-NLS1 RPS17 using three different doses (green [47 µM], red [95 µM], and blue [190 µM]). FIG. 7B shows Kaplan-Meier survival curves of the experiment shown in FIG. 7A.

FIG. 8A shows the tumor growth in response to CA-NLS3 RPS17 using three different doses (green [47 µM], red [95 µM], and blue [190 µM]). FIG. 8B shows Kaplan-Meier survival curves of the experiment shown in FIG. 8A.

STATEMENT REGARDING THE SEQUENCE LISTING

Figure 1A:
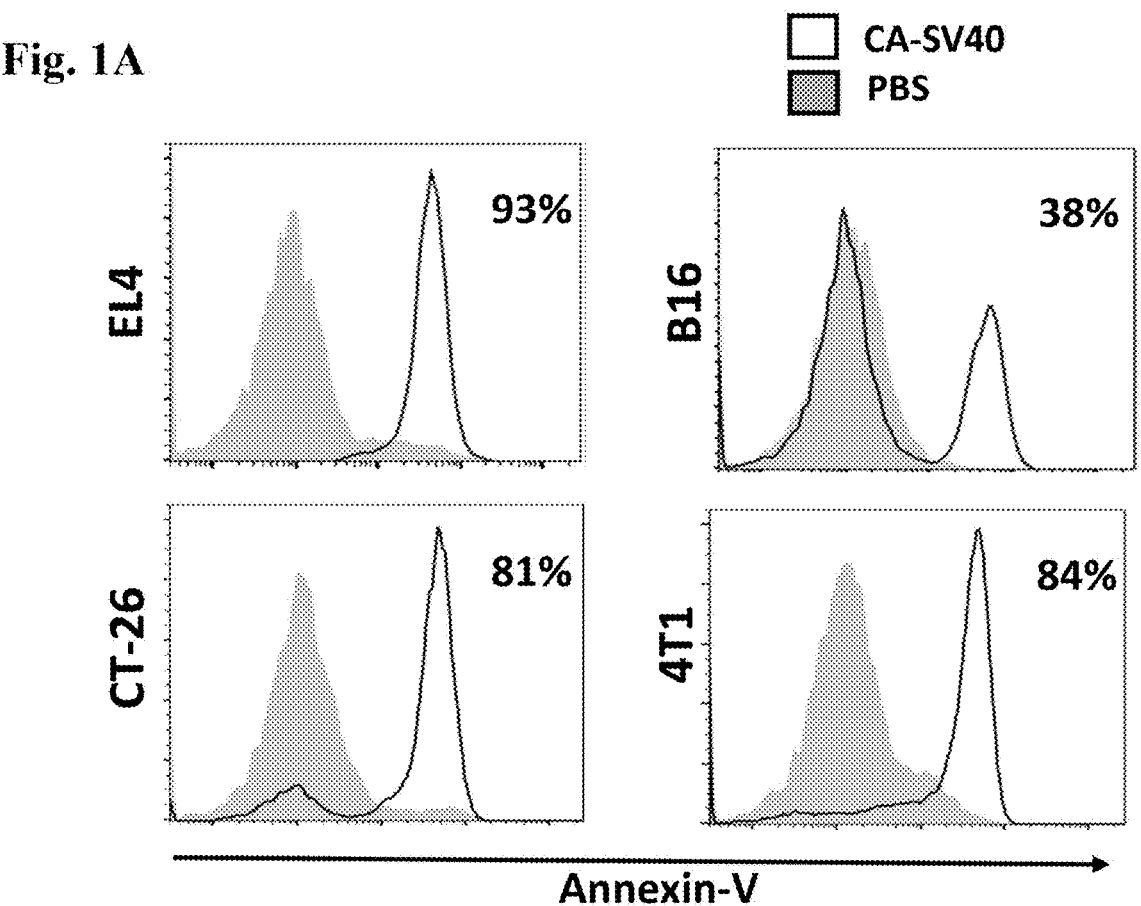
FIGS. 1A to 1C show the results of the cytotoxic effect of CA-SV40 on different cancer cell lines and normal cells.

The Sequence Listing associated with this application is provided in xml format in lieu of a paper copy, and is hereby incorporated by reference into the specification. The name of the file containing the Sequence Listing is 250118_402_USPC_SEQUENCE_LISTING.xml. The xml file size is 15000 bytes, was created on Mar. 10, 2023 and is being submitted electronically via EFS-Web.

| SEQ ID NO: | Description |
|---|---|
| 1 | CA-SV40 |
| 2 | NLS from SV-40 large T-antigen |
| 3 | GWG-SV40NLS |
| 4 | hnRNPA1 M9 NLS |
| 5 | hnRNP D NLS |
| 6 | hnRNP M NLS |
| 7 | PQBP-1 NLS |
| 8 | NLS2-RG Domain RPS17 |
| 9 | NLS1 RPS17 |
| 10 | NLS2 RPS17 |
| 11 | NLS3 RPS17 |
| 12 | cMyc NLS |
| 13 | HuR NLS |
| 14 | Tus NLS |
| 15 | Nucleoplasmin NLS |

DETAILED DESCRIPTION

Described herein are agents having cytotoxic activity, as well as compositions, uses, and methods relating thereto. The cytotoxic agents described herein may include a steroid acid-peptide conjugate or moiety as an active ingredient (e.g., cytotoxic or cytostatic agent) in an amount sufficient to induce killing or inhibition of proliferation of mammalian cells. In some aspects, the present invention stems from the demonstration herein that free steroid acid-peptide conjugates exhibit markedly higher cytotoxic activity in vitro and in vivo on a variety of different cell types, as compared to unconjugated steroid acid or peptide molecules administered separately, or as compared to steroid acid-peptide conjugates that are non-releasably tethered to a carrier molecule such as a recombinant protein.

In some aspects, described herein is a pharmaceutical composition comprising a steroid acid-peptide conjugate having cytotoxic or cytostatic activity, the conjugate being free or releasably bound to a carrier molecule. In some embodiments, the peptide may comprise a protein transduction domain that stimulates endocytosis and/or endosomal formation; comprises a subcellular targeting signal; is a cationic peptide (e.g., a non-cell-penetrating cationic peptide); is a non-immunogenic peptide; or any combination thereof. In some embodiments, the peptide is or comprises a nuclear localization signal (NLS) that mediates nuclear accumulation of free steroid acid-peptide conjugate upon intracellular delivery.

In some aspects, the steroid acid-peptide conjugate may be releasably bound to a carrier molecule. Upon administration of the steroid acid-peptide conjugate linked to the carrier molecule, the steroid-acid peptide conjugate may be released from the carrier molecule. The carrier molecule may be a protein carrier (e.g., antibody or receptor ligand); polysaccharide carrier; polynucleotide carrier (e.g., aptamer); polynucleotide analog carrier; polyethylene glycol carrier; lipid carrier; or other biocompatible carrier. Advantageously, when a carrier molecule (e.g., a protein carrier such as an antibody) is conjugated to a steroid acid-peptide conjugate described herein, the steroid acid-peptide conjugate may exhibit diminished cytotoxic activity. However, upon release of the steroid acid-peptide conjugate from the carrier molecule, the free steroid acid-peptide conjugate may exhibit increased cytotoxic activity.

In some embodiments, the carrier molecule is not a polypeptide antigen and the pharmaceutical composition does not comprise an adjuvant that induces an immune response to the carrier molecule.

In some aspects, the carrier molecule is a targeting molecule. The carrier or target molecule may therefore transport the steroid acid-peptide conjugate to a specific target (e.g., cell or tissue), whereby the steroid acid-peptide conjugate is released from the carrier molecule upon (or subsequently to) binding of the carrier molecule to a specific target or upon internalization of the complex. For example, the carrier may be a targeting molecule, such as an antibody, which targets a specific cell type, tissue, or a tumor. Examples of antibodies include but are not limited to monoclonal antibodies against B cells (e.g., anti-CD20 [rituximab, ocrelizumab, ofatumumab, or obinutuzumab]) or T cells. In some embodiments, the carrier molecule may be a therapeutic monoclonal antibody, such as 3F8, Abagovomab, Abituzumab, Adecatumumab, Alemtuzumab, Altumomab, Amatuximab, Amivantamab, Anatumomab, Arcitumomab, Ascrinvacumab, Atezolizumab, Balstilimab, Bavituximab, Bectumomab, Belantamab, Bevacizumab, Bivatuzumab, Blinatumomab, Botensilimab, Brentuximab, Brontictuzumab, Cantuzumab, Cantuzumab, Capromab, Carotuximab, Catumaxomab, Cetuximab, Cirmtuzumab, Citatuzumab, Cixutumumab, Clivatuzumab, Cofetuzumab, Conatumumab, Dacetuzumab, Dalotuzumab, Daratumumab, Demcizumab, Denintuzumab, Depatuxizumab, Derlotuximab, Detumomab, Dinutuximab, Drozitumab, Duligotumab, Dusigitumab, Duvortuxizumab, Ecromeximab, Edrecolomab, Elotuzumab, Emactuzumab, Emibetuzumab, Enfortumab, Enoblituzumab, Enoticumab, Ensituximab, Ertumaxomab, Etaracizumab, Farletuzumab, Ficlatuzumab, Figitumumab, Flanvotumab, Flotetuzumab, Futuximab, Ganitumab, Gemtuzumab, Girentuximab, Glembatumumab, Ibritumomab, Icrucumab, Igovomab, Imgatuzumab, Indatuximab, Inotuzumab, Intetumumab, Ipilimumab, Iratumumab, Isatuximab, Istiratumab, Labetuzumab, Lexatumumab, Lifastuzumab, Lilotomab, Lintuzumab, Loncastuximab, Lorvotuzumab, Lucatumumab, Lumretuzumab, Mapatumumab, Margetuximab, Matuzumab, Milatuzumab, Minretumomab, Mitumomab, Moxetumomab, Nacolomab, Naptumomab, Narnatumab, Naxitamab, Necitumumab, Nesvacumab, Nimotuzumab, Nivolumab, Nofetumomab, Obinutuzumab, Ocaratuzumab, Ofatumumab, Olaratumab, Onartuzumab, Ontuxizumab, Onvatilimab, Opicinumab, Oportuzumab, Oportuzumab, Oregovomab, Oregovomab, Orticumab, Otelixizumab, Otilimab, Otlertuzumab, Otlertuzumab, Oxelumab, Ozanezumab, Ozoralizumab, Pagibaximab, Palivizumab, Pamrevlumab, Panitumumab, Panitumumab, Pankomab, Pankomab, Panobacumab, Parsatuzumab, Parsatuzumab, Pascolizumab, Pasotuximab, Pateclizumab, Patritumab, Patritumab, PDR001, Pembrolizumab, Pembrolizumab, Pemtumomab, Pemtumomab, Perakizumab, Pertuzumab, Pertuzumab, Pexelizumab, Pidilizumab, Pinatuzumab, Pinatuzumab, Pintumomab, Pintumomab, Placulumab, Plozalizumab, Pogalizumab, Polatuzumab, Polatuzumab, Ponezumab, Porgaviximab, Prasinezumab, Prezalizumab, Prezalumab, Priliximab, Pritoxaximab, Pritumumab, Pritumumab, PRO, Quilizumab, Racotumomab, Racotumomab, Radretumab, Radretumab, Rafivirumab, Ralpancizumab, Ramucirumab, Ramucirumab, Ranevetmab, Ranibizumab, Ravagalimab, Ravulizumab, Raxibacumab, Refanezumab, Regavirumab, Regdanvimab, Relatlimab, Remtolumab, Reslizumab, Rilotumumab, Rilotumumab, Rinucumab, Risankizumab, Rituximab, Rituximab, Rivabazumab, Rmab, Robatumumab, Robatumumab, Roledumab, Romilkimab, Romosozumab, Rontalizumab, Rosmantuzumab, Rosmantuzumab, Rovalpituzumab, Rovalpituzumab, Rovelizumab, Rozanolixizumab, Ruplizumab, SA237, Sacituzumab, Sacituzumab, Samalizumab, Samrotamab, Sarilumab, Satralizumab, Satumomab, Satumomab, Secukinumab, Selicrelumab, Seribantumab, Seribantumab, Setoxaximab, Setrusumab, Sevirumab, SGN-CD19A, SHP647, Sibrotuzumab, Sibrotuzumab, Sifalimumab, Siltuximab, Siltuximab, Simtuzumab, Simtuzumab, Siplizumab, Sirtratumab, Sirukumab, Sofituzumab, Sofituzumab, Solanezumab, Solitomab, Solitomab, Sonepcizumab, Sontuzumab, Sotrovimab, Spartalizumab, Spesolimab, Stamulumab, Sulesomab, Suptavumab, Sutimlimab, Suvizumab, Suvratoxumab, Tabalumab, Tacatuzumab, Tacatuzumab, Tadocizumab, Tafasitamab, Talacotuzumab, Talizumab, Talquetamab, Tamtuvetmab, Tanezumab, Taplitumomab, Taplitumomab, Tarextumab, Tarextumab, Tavolimab, Teclistamab, Tefibazumab, Telimomab, Telisotuzumab, Telisotuzumab, Tenatumomab, Tenatumomab, Teneliximab, Teplizumab, Tepoditamab, Teprotumumab, Teprotumumab, Tesidolumab, Tetulomab, Tezepelumab, TGN1412, Tibulizumab, Tigatuzumab, Tigatuzumab, Tildrakizumab, Timigutuzumab, Timolumab, tiragolumab, Tiragotumab, Tislelizumab, Tisotumab, Tisotumab, Tixagevimab, TNX-650, Tocilizumab, Tomuzotuximab, Toralizumab, Tosatoxumab, Tositumomab, Tositumomab, Tovetumab, Tovetumab, Tralokinumab, Trastuzumab, Trastuzumab, Trastuzumab, Trastuzumab, TRBS07, Tregalizumab, Tremelimumab, Trevogrumab, Tucotuzumab, Tucotuzumab, Tuvirumab, Ublituximab, Ublituximab, Uloculplumab, Urelumab, Urtoxazumab, Ustekinumab, Utomilumab, Vadastuximab, Vanalimab, Vandortuzumab, Vandortuzumab, Vantictumab, Vantictumab, Vanucizumab, Vanucizumab, Vapaliximab, Varisacumab, Varlilumab, Vatelizumab, Vedolizumab, Veltuzumab, Veltuzumab, Vepalimomab, Vesencumab, Visilizumab, Vobarilizumab, Volociximab, Vonlerolizumab, Vopratelimab, Vorsetuzumab, Vorsetuzumab, Votumumab, Votumumab, Vunakizumab, Xentuzumab, XMAB-5574, Zalutumumab, Zalutumumab, Zanolimumab, Zatuximab, Zenocutuzumab, Ziralimumab, Zolbetuximab, or Zolimomab.

In some aspects, the carrier molecule is releasably bound to the steroid acid-peptide conjugate via a releasable linker. In some embodiments, the releasable linker may be a cleavable linker (such as an enzymatically cleavable linker, e.g., via cathepsin—[e.g., cathepsin B], valine-citrulline, or matrix metalloproteinase-mediated cleavage), a photocleavable linker, a redox-sensitive linker (e.g., disulfide link or bond), or a pH-sensitive linker (e.g., hydrazine linked). For example, the extracellular environments surrounding certain tissues may consist of reducing agents which destroy the link between the steroid-acid peptide conjugate and the carrier molecule. In other scenarios, internalization of the steroid acid-peptide conjugate linked to the carrier molecule may destroy the linker via lowering of the pH in the endosome. Furthermore, tumor microenvironments may have a more acidic pH due to increased growth and metabolism and subsequent accumulation of lactic acid. In some scenarios, certain tumors may secrete proteases which cleave the linker between the steroid acid-peptide conjugate and the carrier molecule. Nevertheless, upon release of the steroid acid-peptide conjugate from the carrier molecule, the steroid acid-peptide may exert its cytotoxic activity.

In some aspects, the steroid acid-peptide conjugate may be bound to a carrier molecule that includes an antibody bound to a further cytotoxic agent or drug (such a chemotherapeutic drug or agent). In some embodiments, the steroid acid-peptide conjugate is bound to one or more antibody-drug conjugates [ADCs]. Antibody binding to the further cytotoxic agent or drug may be releasable (e.g., cleavable) or non-releasable (e.g., non-cleavable).

In some embodiments, the bile acid-peptide conjugate may be the only cytotoxic or cytostatic agent releasably bound to the carrier molecule described herein. In some embodiments, the bile acid-peptide conjugate may be the only cytotoxic or cytostatic agent comprised in the pharmaceutical composition described herein.

In some aspects, free or releasably bound steroid acid-peptide conjugate may be administered alone directly into a specific microenvironment. For example, the steroid acid-peptide conjugate may be locally administered into the skin (e.g., subcutaneous injection) or intratumorally.

In some embodiments, the steroid acid moiety may enhance endocytosis and/or endosomal escape when internalized. Without being bound by theory, steroid acids (e.g., bile acids and bile acid analogs) have been shown to be utilized/exploited by viruses to facilitate their infection of host cells, such as by increasing their endocytic uptake and/or endosomal escape to gain access to the cytosol (Shivanna et al., 2014; Shivanna et al., 2015; Murakami et al., 2020). For example, bile acids have been shown to trigger the enzyme acid sphingomyelinase (ASM) to cleave sphingomyelin to ceramide on the inner leaflet of endosomes. Increased amounts of ceramide destabilize membranes and facilitate endosomal escape. In some embodiments, steroid acids described herein comprise those that trigger ceramide accumulation on the inner leaflet of endosomes, thereby destabilizing endosomal membranes and facilitating endosomal escape of the steroid acid upon intracellular delivery. In some embodiments, steroid acids described herein comprise those that trigger increased acid sphingomyelinase (ASM)-mediated cleavage of sphingomyelin to form ceramide.

In some embodiments, the steroid acid described herein comprises or consists of a bile acid (e.g., a primary bile acid or a secondary bile acid). In some embodiments, the steroid acid may be or comprise: cholic acid (CA), chenodeoxycholic acid (CDCA), deoxycholic acid (DCA), lithocholic acid (LCA), glycodeoxycholic acid (GDCA), glycocholic acid (GCA), taurocholic acid (TCA), glycodeoxycholic acid (CDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), glycoursodeoxycholic acid (GUDCA), or any analog thereof that: induces endocytosis; triggers ceramide accumulation on the inner leaflet of endosomes; triggers increased acid sphingomyelinase (ASM)-mediated cleavage of sphingomyelin to form ceramide; and/or has a hydrophobicity greater than that of cholic acid.

Hydrophobic bile acids such as GCDCA, TCA, GCA, and CA (but not hydrophilic bile acids such as UDCA) were shown to increase GII.3 human norovirus infection and replication in host intestinal cells by enhancing endosomal uptake and endosomal escape via ASM-mediated ceramide accumulation on the apical membrane (Murakami et al., 2020). In some embodiments, the steroid acid described herein comprises or consists of a bile acid or bile acid analog that is more hydrophobic than cholic acid. In some embodiments, the steroid acid described herein comprises or consists of a bile acid or bile acid analog that is more hydrophobic than cholic acid (e.g., CDCA, DCA, LCA, TCA, TDCA, TCDCA, GCA, GDCA, or GCDCA; Hanafi et al., 2018).

In some embodiments, the steroid acid-peptide conjugate described herein is not or does not include cholic acid. In some embodiments, the NLS peptide described herein is not or does not comprise an SV40 NLS. In some embodiments, the steroid acid-peptide conjugate described herein is not or does not comprise CA-SV40.

In some embodiments, the steroid acid may be conjugated to the peptide, for example at or towards a free N-terminal or C-terminal amino group of the peptide or at some other functional group within the peptide.

In some embodiments, the peptide may be a non-immunogenic peptide. In some embodiments, the peptide may be a water-soluble peptide, wherein conjugation of the peptide to the steroid acid increases the water solubility of the steroid acid-peptide moiety as compared to the steroid acid moiety alone. In some embodiments, the peptide may be a cationic peptide.

In some embodiments, the peptide may comprise one or more domains that impart an additional functionality to the peptide in the steroid acid-peptide conjugates described herein. As used herein, a "domain" generally refers to a part of a protein having a particular functionality. Some domains conserve their function when separated from the rest of the protein, and thus can be used in a modular fashion. The modular characteristic of many protein domains can provide flexibility in terms of their placement within the peptides described herein. However, some domains may perform better when engineered at certain positions of the peptide (e.g., at the N- or C-terminal region, or therebetween). The position of the domain within its endogenous protein may be an indicator of where the domain should be engineered within the peptide.

In some embodiments where non-specific delivery may be desired, the peptide may comprise a protein transduction domain (PTD) that stimulates endocytosis, endosomal formation, or intracellular delivery in a non-cell-specific manner. In some embodiments, the peptide may comprise a subcellular targeting signal promoting targeting of the steroid acid-peptide conjugate described herein to a specific subcellular compartment. In some embodiments, the peptide may comprise a nuclear localization signal (NLS) that targets the steroid acid-peptide conjugate to the nucleus.

In some embodiments, the nuclear localization signals described herein may comprise or be derived from the NLS from SV-40 large T-antigen (e.g., PKKKRKV; SEQ ID NO: 1 or 2) or from other classical NLSs. In some embodiments, the nuclear localization signals described herein may comprise or be derived from non-classical NLS (e.g., acidic M9 domain in the hnRNP A1 protein; the sequence KIPIK in yeast transcription repressor Matα2; PY-NLS; ribosomal NLS; or the complex signals of U snRNPs). In some embodiments, the nuclear localization signal described herein comprises or consists essentially of the amino acid sequence of any one of SEQ ID NOs: 1 to 15, or any portion thereof. In some embodiments, the nuclear localization signal described herein comprises or consists essentially of a nuclear localisation signal which is SV40 NLS (e.g., comprised in SEQ ID NO: 1 or 2), GWG-SV40 NLS (e.g., comprised in SEQ ID NO: 3), hnRNPA1 M9 NLS (e.g., comprised in SEQ ID NO: 4), hnRNP D NLS (e.g., comprised in SEQ ID NO: 5), hnRNP M NLS (e.g., comprised in SEQ ID NO: 6), PQBP-1 NLS (e.g., comprised in SEQ ID NO: 7), NLS2-RG Domain RPS17 (e.g., comprised in SEQ ID NO: 8), NLS1 RPS17 (e.g., comprised in SEQ ID NO: 9), NLS2 RPS17 (e.g., comprised in SEQ ID NO: 10), NLS3 RPS17 (e.g., comprised in SEQ ID NO: 11), cMyc NLS (e.g., comprised in SEQ ID NO: 12), HuR NLS (e.g., comprised in SEQ ID NO: 13), Tus NLS (e.g., comprised in SEQ ID NO: 14), or Nucleoplasmin NLS (e.g., comprised in SEQ ID NO: 15). In some instances, the SEQ ID NOs referred to above comprise an N-terminal cysteine residue that was used to facilitate conjugation to the carrier molecule (e.g., the thiol group of the N-terminal cysteine residue). Thus, in some embodiments, the NLS sequences referred to herein may exclude the N-terminal cysteine residue comprised in any one of SEQ ID NOs: 1 to 15. In some embodiments, other functional groups added or inserted (e.g., towards the N to C terminal portions of the peptides described herein) to facilitate steroid acid-peptide conjugation to a given carrier molecule are also envisaged (e.g., carboxyl groups, synthetic amino acids, etc.). For example, the peptide may include a C-term amide and/or an N-term cysteine. In some embodiments, peptide does not comprise an endosomal escape motif, or protein transduction, or cell penetrating motif.

In some embodiments, the nuclear localization signals described herein may comprise the general consensus sequence: (i) K(K/R)X(K/R); (ii) (K/R)(K/R)X$_{10-12}$(K/R)$_{3/5}$, wherein (K/R)$_{3/5}$ represents three lysine or arginine residues out of five consecutive amino acids; (iii) KRX$_{10-12}$KRRK; (iv) KRX$_{10-12}$K(K/R)(K/R); or (v) KRX$_{10-12}$K(K/R)X(K/R), wherein X is any amino acid (Sun et al., 2016).

In some embodiments, the peptide does not include an endosomal escape motif (e.g. -GFFG, -GWG, -GFWG, -GFWFG, -GWWG, -GWGGWG, and -GWWWG), or protein transduction, or cell penetrating motif (such as a cell penetrating peptide).

In some embodiments, the free steroid acid-peptide conjugates described herein possess cytotoxic or cytostatic activity against mammalian cells, such as but not limited to immune cells or tumor/cancer cells. In some cases, induction of cytotoxicity is exhibited via induction of a mechanism of cell death. In some cases, the steroid acid-peptide conjugates described herein induce apoptosis or late apoptosis in cells. In some cases, the steroid acid-peptide conjugates described herein induce activation of the reactive oxygen species (ROS) pathway or release of intracellular ROS.

In some embodiments, the steroid acid-peptide conjugate is used or is present in a composition described herein at an effective concentration of at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, or 500 micromolar. As used herein, the term "effective concentration" refers to the concentration of free or freeable steroid acid-peptide conjugate. For example, when the steroid acid-peptide conjugate is present as free molecules that are not bound to a carrier molecule, the effective concentration is the concentration of free of the steroid acid-peptide conjugate molecules. For example, when the steroid acid-peptide conjugate is releasably bound to a carrier molecule, then the effective concentration of the steroid-acid peptide conjugate refers to the concentration of the released steroid acid-peptide conjugate.

In some embodiments, the composition may further comprise any pharmaceutically or physiologically acceptable carrier, adjuvant, and/or excipient. In some embodiments, the composition or steroid acid-peptide conjugate may be formulated within a hydrogel, liposome, or nanoparticle (e.g., lipid nanoparticle). In some embodiments, prodrugs of the steroid acid-peptide conjugates (free or releasably bound to a carrier molecule) are contemplated herein and may be encompassed in the expression "steroid acid-peptide conjugate", to the extent that administration of the prodrug results in generation of a steroid acid-peptide conjugate described herein in vivo.

In some aspects, described herein is a method for treating cancer, proliferative disease, or any other disease or disorder ameliorated by treatment with an antiproliferative drug in a subject (e.g., human), the method including administering the pharmaceutical composition or steroid acid-peptide conjugate as defined herein to the subject. The cancer may include any cancer such as but not limited to breast, colon, prostate, blood, lymphoma, lung, skin, brain, pancreatic, kidney, liver, cancer or any cancer of a tissue or organ. In some aspects, the cancer may include a solid or liquid tumor.

In some aspects, described herein is a method for treating an autoimmune disease in a subject (e.g., human), the method including administering the pharmaceutical composition or steroid acid-peptide conjugate as defined herein to the subject. In some embodiments, the autoimmune disease may include but is not limited to multiple sclerosis, rheumatoid arthritis, or systemic lupus erythematosus.

In some aspects, the method described herein includes combining the pharmaceutical composition or steroid acid-peptide conjugate with any known drug for the treatment of said cancer or autoimmune disease or in combination with standard-of-care, such as but not limited to immunosuppressive drugs, immune-checkpoint inhibitors, or chemotherapies. In some aspects, the composition or conjugate is at a dose of at least 0.5, 1, 2, 3, 4, 5, 10, 25, 50, 75, 100, 125, 150, 175, 200, 250, 300, 350, 400, 450, or 500 mg/kg.

In some aspects, described herein is a use the pharmaceutical composition or steroid acid-peptide conjugate as defined herein, for treating cancer, an autoimmune disease, proliferative disease, or any other disease or disorder ameliorated by treatment with an antiproliferative drug in a subject. Although cancers and autoimmune diseases are described herein as examples, the pharmaceutical composition or steroid acid-peptide conjugate defined herein can be used for the treatment of any disease or disorder requiring targeted killing (e.g., cytotoxicity) of a specific cell type.

In some embodiments, the methods and uses described herein include any route of administration, such as but not limited to oral, intravenous, intranasal, intramuscular, subcutaneous, intradermal, intratumoral, intracranial, topical, and intrarectal administration.

Items

In some aspects, described herein are one or more of the following items:

1. A pharmaceutical composition comprising a steroid acid-peptide conjugate having cytotoxic or cytostatic activity, the conjugate being free or releasably bound to a carrier molecule.
2. The pharmaceutical composition of item 1, wherein the peptide: (i) comprises a protein transduction domain that stimulates endocytosis and/or endosomal formation; (ii) comprises a subcellular targeting signal; (iii) is a cationic peptide (e.g., a non-cell-penetrating cationic peptide); (iv) is a non-immunogenic peptide; or (v) any combination of (i) to (iv).

3. The pharmaceutical composition of item 1 or 2, wherein the carrier molecule is a targeting molecule, and wherein the steroid acid-peptide conjugate is released from the carrier molecule upon (or subsequent to) binding of the carrier molecule to a specific target.
4. The pharmaceutical composition of any one of items 1 to 3, wherein the carrier molecule is a protein carrier (e.g., antibody or receptor ligand); polysaccharide carrier; polynucleotide carrier; polynucleotide analog carrier; polyethylene glycol carrier; lipid carrier; or other biocompatible carrier.
5. The pharmaceutical composition of any one of items 1 to 4, wherein the conjugate is releasably bound to the carrier molecule via a cleavable linker (e.g., enzymatically cleavable, such as cathepsin-, matrix metalloproteinase-mediated cleavage, or a valine-citrulline linker), photocleavable linker, a redox-sensitive linker (e.g., disulfide link), or a pH-sensitive linker.
6. The pharmaceutical composition of any one of items 1 to 5, wherein the carrier molecule is an antibody or receptor ligand.
7. The pharmaceutical composition of any one of items 1 to 6, wherein: (a) the steroid acid-peptide conjugate is the only cytotoxic or cytostatic agent releasably bound to the carrier molecule; (b) the steroid acid-peptide conjugate is the only cytotoxic or cytostatic agent comprised in the pharmaceutical composition; or both (a) and (b).
8. The pharmaceutical composition of item 6, wherein the antibody is further bound to a further cytotoxic agent or drug (e.g., antibody-drug conjugates [ADCs]), wherein the binding of the antibody to the further cytotoxic agent or drug is releasable (e.g., cleavable) or non-releasable (e.g., non-cleavable).
9. The pharmaceutical composition of any one of items 1 to 8, wherein the steroid acid is a bile acid.
10. The pharmaceutical composition of any one of items 1 to 9, wherein the steroid acid is a primary bile acid or a secondary bile acid.
11. The pharmaceutical composition of any one of items 1 to 10, wherein the steroid acid is or comprises: (a) a bile acid which is: cholic acid (CA), chenodeoxycholic acid (CDCA), deoxycholic acid (DCA), lithocholic acid (LCA), glycodeoxycholic acid (GDCA), glycocholic acid (GCA), taurocholic acid (TCA), glycodeoxycholic acid (CDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), or glycoursodeoxycholic acid (GUDCA); (b) an analog of the bile acid of (a) that: induces endocytosis; triggers ceramide accumulation on the inner leaflet of endosomes; triggers increased acid sphingomyelinase (ASM)-mediated cleavage of sphingomyelin to form ceramide; and/or has a hydrophobicity greater than that of cholic acid; (c) a bile acid or bile acid analog that is more hydrophobic than cholic acid (e.g. CDCA, DCA, LCA, TCA, TDCA, TCDCA, GCA, GDCA, or GCDCA); or (d) any combination of (a) to (c).
12. The pharmaceutical composition of any one of items 1 to 11, wherein: the steroid acid is not or does not comprise cholic acid; the NLS peptide is not or does not comprise an SV40 NLS; and/or the steroid acid-peptide conjugate is not or does not comprise CA-SV40.
13. The pharmaceutical composition of any one of items 1 to 12, wherein the steroid acid is conjugated at or towards the N- or C-terminus of the peptide.
14. The pharmaceutical composition of any one of items 1 to 13, wherein the peptide is or comprises a nuclear localization signal which is a classical NLS (e.g., NLS from SV-40 large T-antigen (e.g., PKKKRKV; SEQ ID NO: 1 or 2) or from other classical NLSs) or a non-classical NLS (e.g., acidic M9 domain in the hnRNP A1 protein; the sequence KIPIK in yeast transcription repressor Matα2; PY-NLS; ribosomal NLS; and the complex signals of U snRNPs).
15. The pharmaceutical composition of any one of items 1 to 14, wherein the peptide is or comprises a nuclear localization signal which is a/an: SV40 NLS (e.g., comprised in SEQ ID NO: 1 or 2), GWG-SV40NLS (e.g., comprised in SEQ ID NO: 3), hnRNPA1 M9 NLS (e.g., comprised in SEQ ID NO: 4), hnRNP D NLS (e.g., comprised in SEQ ID NO: 5), hnRNP M NLS (e.g., comprised in SEQ ID NO: 6), PQBP-1 NLS (e.g., comprised in SEQ ID NO: 7), NLS2-RG Domain RPS17 (e.g., comprised in SEQ ID NO: 8), NLS1 RPS17 (e.g., comprised in SEQ ID NO: 9), NLS2 RPS17 (e.g., comprised in SEQ ID NO: 10), NLS3 RPS17 (e.g., comprised in SEQ ID NO: 11), cMyc NLS (e.g., comprised in SEQ ID NO: 12), HuR NLS (e.g., comprised in SEQ ID NO: 13), Tus NLS (e.g., comprised in SEQ ID NO: 14), or Nucleoplasmin NLS (e.g., comprised in SEQ ID NO: 15), or is a variant of an NLS having nuclear localization activity, the NLS comprising or consisting of the amino acid sequence of any one of SEQ ID NOs: 1 to 15.
16. The pharmaceutical composition of any one of items 1 to 15, wherein the peptide does not comprise an endosomal escape motif, or protein transduction motif, or cell penetrating motif.
17. The pharmaceutical composition of any one of items 1 to 16, which comprises an effective concentration of the steroid acid-peptide conjugate of at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, or 500 micromolar.
18. The pharmaceutical composition of any one of items 1 to 17, wherein the composition or conjugate is formulated within a hydrogel, liposome, or nanoparticle (e.g., lipid nanoparticle).
19. The pharmaceutical composition of any one of items 1 to 18, further comprising pharmaceutically or physiologically acceptable carrier, adjuvant, and/or excipient.
20. The pharmaceutical composition of any one of items 1 to 19, for use in the treatment of cancer, an autoimmune disease, or any other disease or disorder ameliorated by treatment with an antiproliferative drug in a subject; or for use as a cytotoxic or cytostatic agent.
21. The pharmaceutical composition for use of item 20, in combination with immune-checkpoint inhibitor or immunosuppressive therapy.
22. The pharmaceutical composition for use of item 20 or 21, wherein the composition or conjugate is at a dose of at least 0.5, 1, 2, 3, 4, 5, 10, 25, 50, 75, 100, 125, 150, 175, 200, 250, 300, 350, 400, 450, or 500 mg/kg.
23. The pharmaceutical composition for use of any one of items 20 to 22, wherein the composition or conjugate is adapted or formulated for oral, intravenous, intranasal, intramuscular, subcutaneous, intradermal, intratumoral, intracranial, topical, intrarectal administration, or any other route of administration.
24. A method for treating cancer or any other disease or disorder ameliorated by treatment with an antiproliferative drug in a subject, the method comprising administering a cytotoxic or cytostatic dose of the pharmaceutical composition or steroid acid-peptide conjugate as defined in any one of items 1 to 19, to the subject.
25. The method of item 24, wherein the method is combined with immune-checkpoint inhibitor therapy.
26. The method of item 24 or 25, wherein the composition or conjugate is at a dose of at least 0.5, 1, 2, 3, 4, 5, 10, 25, 50, 75, 100, 125, 150, 175, 200, 250, 300, 350, 400, 450, or 500 mg/kg.
27. A method for treating an autoimmune disease in a subject, the method comprising administering a cytotoxic or cytostatic dose of the pharmaceutical composition or steroid acid-peptide conjugate as defined in any one of items 1 to 19, to the subject.
28. The method of item 27, wherein the method is combined with immunosuppressive therapy.
29. The method of item 27 or 28, wherein the composition or conjugate is at a dose of at least 0.5, 1, 2, 3, 5, 10, 25, 50, 75, 100, 125, 150, 175, 200, 250, 300, 350, 400, 450, or 500 mg/kg.
30. The method of any one of items 24 to 29, wherein the administration comprises oral, intravenous, intranasal, intramuscular, subcutaneous, intradermal, intratumoral, intracranial, topical, intrarectal administration, or any other route of administration.
31. Use the pharmaceutical composition or steroid acid-peptide conjugate as defined in any one of items 1 to 19, for treating cancer, an autoimmune disease, or any other disease or disorder ameliorated by treatment with an antiproliferative drug in a subject; or as a cytotoxic or cytostatic agent.
32. The use of item 31, in combination with immune-checkpoint inhibitor or immunosuppressive therapy.
33. The use of item 31 or 32, wherein the composition or conjugate is at a dose of at least 0.5, 1, 2, 3, 4, 5, 10, 25, 50, 75, 100, 125, 150, 175, 200, 250, 300, 350, 400, 450, or 500 mg/kg.
34. The use of any one of items 31 to 33, wherein the composition or conjugate is adapted for oral, intravenous, intranasal, intramuscular, subcutaneous, intradermal, intratumoral, intracranial, topical, intrarectal administration, or any other route of administration.
35. A pharmaceutical composition comprising a bile acid-peptide conjugate as a cytotoxic or cytostatic agent, the conjugate being free or releasably bound to a carrier molecule and being present in the pharmaceutical composition at an effective concentration of at least 40 micromolar, wherein the peptide comprised in the bile acid-peptide conjugate comprises a nuclear localization signal (NLS), and wherein the bile acid-peptide conjugate is releasably bound to the carrier molecule via an enzymatically cleavable linker, a photocleavable linker, a redox-sensitive linker, or a pH-sensitive linker.
36. The pharmaceutical composition of item 35, wherein the effective concentration of the bile acid-peptide conjugate in the pharmaceutical composition is at least 60 micromolar.
37. The pharmaceutical composition of item 35, wherein the effective concentration of the bile acid-peptide conjugate in the pharmaceutical composition is at least 80 micromolar.
38. The pharmaceutical composition of item 35, wherein the effective concentration of the bile acid-peptide conjugate in the pharmaceutical composition is at least 100 micromolar.
39. The pharmaceutical composition of item 35, wherein the effective concentration of the bile acid-peptide conjugate in the pharmaceutical composition is at least 150 micromolar.
40. The pharmaceutical composition of any one of items 35 to 39, wherein the bile acid is: cholic acid (CA), chenodeoxycholic acid (CDCA), deoxycholic acid (DCA), lithocholic acid (LCA), glycodeoxycholic acid (GDCA), glycocholic acid (GCA), taurocholic acid (TCA), glycodeoxycholic acid (CDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), or glycoursodeoxycholic acid (GUDCA).
41. The pharmaceutical composition of any one of items 35 to 39, wherein the bile acid is an analog of CA, CDCA, DCA, LCA, GDCA, GCA, TCA, CDCA, GCDCA, TDCA, GLCA, TLCA, THDCA, TCDCA, UCA, TUDCA, UDCA, or GUDCA, wherein the analog: induces endocytosis; triggers ceramide accumulation on the inner leaflet of endosomes; or triggers increased acid sphingomyelinase (ASM)-mediated cleavage of sphingomyelin to form ceramide.
42. The pharmaceutical composition of any one of items 35 to 41, wherein the nuclear localization signal is as define din item 15.
43. The pharmaceutical composition of any one of items 35 to 41, wherein the nuclear localization signal is a variant of an NLS having nuclear localization activity, the NLS comprising or consisting of the amino acid sequence of any one of SEQ ID NOs: 1 to 15.
44. The pharmaceutical composition any one of items 35 to 43, wherein the bile acid-peptide conjugate does not comprise CA-SV40.
45. The pharmaceutical composition of any one of items 35 to 44, comprising the bile acid-peptide conjugate releasably bound to the carrier molecule, wherein the carrier molecule is a targeting molecule that binds to a specific target, and wherein the bile acid-peptide conjugate is released from the targeting molecule upon, or subsequent to, binding of the targeting molecule to its target.
46. The pharmaceutical composition of any one of items 35 to 45, comprising the bile acid-peptide conjugate releasably bound to the carrier molecule, wherein carrier molecule is: a protein carrier; a polysaccharide carrier; a polynucleotide carrier; a polynucleotide analog carrier; a polyethylene glycol carrier; or a lipid carrier.
47. The pharmaceutical composition of any one of items 35 to 46, comprising the bile acid-peptide conjugate releasably bound to the carrier molecule, wherein the carrier molecule is an antibody or a receptor ligand.
48. The pharmaceutical composition of item 47, wherein the bile acid-peptide conjugate is the only cytotoxic or cytostatic agent releasably bound to the carrier molecule.

49. The pharmaceutical composition of item 47, wherein the bile acid-peptide conjugate is the only cytotoxic or cytostatic agent comprised in the pharmaceutical composition.
50. The pharmaceutical composition of any one of items 35 to 49, which comprises the bile acid-peptide conjugate releasably bound to the carrier molecule, wherein the carrier molecule is not a polypeptide antigen and the pharmaceutical composition does not comprise an adjuvant that induces an immune response to the carrier molecule.
51. A method for treating a subject having cancer, the method comprising administering a cytotoxic or cytostatic dose of the pharmaceutical composition of any one of items 35 to 50 to the subject.
52. The method of item 51, further comprising administering an immune-checkpoint inhibitor to the subject.
53. A method for treating an autoimmune disease in a subject, the method comprising administering a cytotoxic or cytostatic dose of the pharmaceutical composition of any one of items 35 to 52 to the subject.
54. The method of item 53, further comprising administering an immunosuppressive agent to the subject.

EXAMPLES

Example 1

General Materials and Methods

Animals and Ethics

Six- to eight-week-old BALB/c mice were purchased from Jackson Laboratories (Bar Harbor, ME, USA) whereas C57BL/6 mice of similar age were purchased from Charles River (Montreal, QC, Canada). Littermate mice were interbred and housed in a pathogen-free environment at the animal facility of the Institute for Research in Immunology and Cancer (IRIC). Animal protocols were approved by the Animal Care Committee of Université de Montréal.

Cell Lines and Reagents

All cell culture media and reagents were purchased from Wisent Bioproducts (St-Bruno, QC, Canada) unless otherwise indicated. All flow cytometry antibodies were purchased from BD Biosciences (San Jose, CA, USA) unless otherwise indicated. The PD-1 antibody (clone RMP1-14) used in in vivo studies was purchased from BioXCell (West Lebanon, NH, USA).

Generation of the Bile Acid-NLS Moieties

Bile acid-NLS moieties were synthesized similar to the synthesis of cholic acid-NLS (ChAcNLS) as previously described in Beaudoin et al., 2016, in U.S. Pat. No. 11,291,717, or in WO/2022/232945, unless otherwise specified. For example, for CA-SV40NLS, cholic acid was conjugated to the free amino group of the N-terminal cysteine residue of a 13-mer peptide (CGYGPKKKRKVGG; SEQ ID NO: 1) that comprises a nuclear localization signal from SV40 large T-antigen (SEQ ID NO: 2) flanked by linker amino acids.

Generation of Bone Marrow Derived DCs

Mouse bone marrow derived DCs (BMDCs) were generated by flushing the whole marrow from mouse femurs using RPMI™ 1640 supplemented with 10% fetal bovine serum (FBS), 50 U/mL Penicillin-Streptomycin, 2 mM L-glutamine, 10 mM HEPES, 1% MEM Non-essential Amino Acids, 1 mM Sodium Pyruvate, 0.5 mM β-mercaptoethanol. Following red blood cell lysis, cells were then cultured in media supplemented with 50 ng/mL murine recombinant GM-CSF. The media was changed on days 2, 4, 6 and 8. On day 9, the media was replaced to include recombinant murine GM-CSF and LPS from *Escherichia coli* O111 (1 ng/mL) to stimulate DC maturation. Mature DCs were assessed by flow cytometry for their surface expression of CD3, CD19, NK1.1, CD11c, CD80, CD86, and I-A$^b$.

Tumor Model

Female C57BL/6 mice (n=10/group) received a SC injection of $5 \times 10^5$ EL4 cells at Day 0. Five days later (appearance of palpable tumors~40-60 mm$^3$), mice were SC-injected with PBS, CA-SV40, anti-PD-1, or anti-CTLA4, alone or in combination.

Statistical Analysis p-values were calculated using the one-way analysis of variance (ANOVA). Results are represented as average mean with S.D. error bars, and statistical significance is represented with asterisks: *P<0.05, P<0.01, *P<0.001.

Example 2

Cholic Acid-SV40 NLS Conjugate Induces Cell Death

Figure 1B:
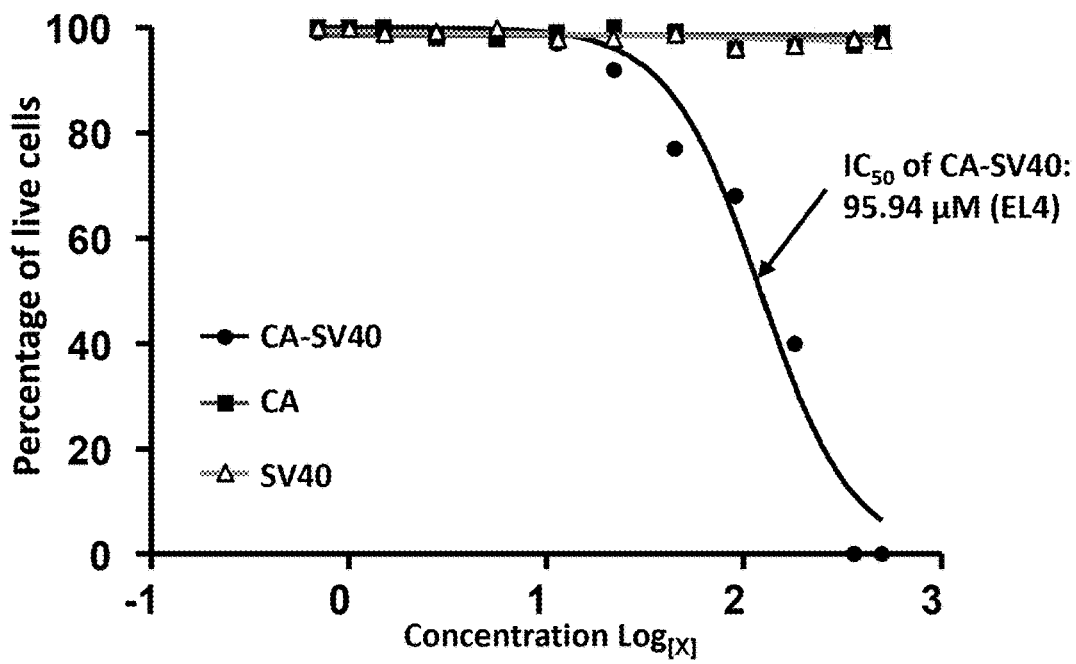
Figure 1C:
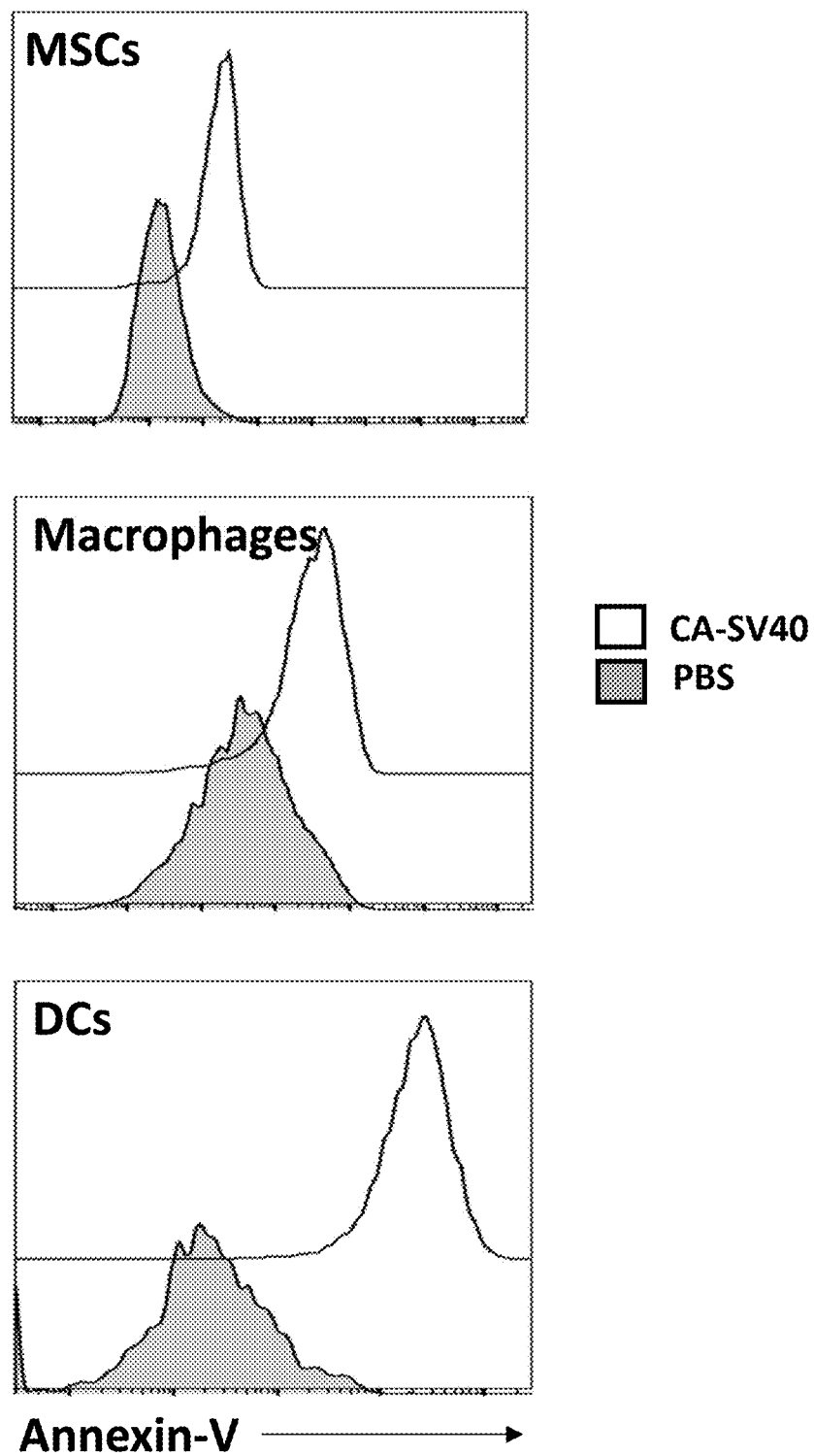

As shown in FIG. 1A, cholic acid (CA) conjugated to the SV40 NLS (CA-SV40) triggers cell death through apoptosis of the T-cell lymphoma line EL4 as well as colon (CT-26) and breast cancer (4T-1) cells to a similar extent, as measured by Annexin V staining. We next conducted a cell death curve analysis by flow cytometry and identified the IC$_{50}$ of CA-SV40 on the EL4 T-cell lymphoma to be 95.94 µM (FIG. 1B). Interestingly, CA and SV40 NLS alone did not exhibit any cytotoxic activity at any of the concentrations tested. Furthermore, CA-SV40 was shown to induce apoptosis in normal or healthy cells, such as in mesenchymal stem cells (MSCs), macrophages, and bone marrow-derived dendritic cells (DCs) (FIG. 1C).

Figure 2A:
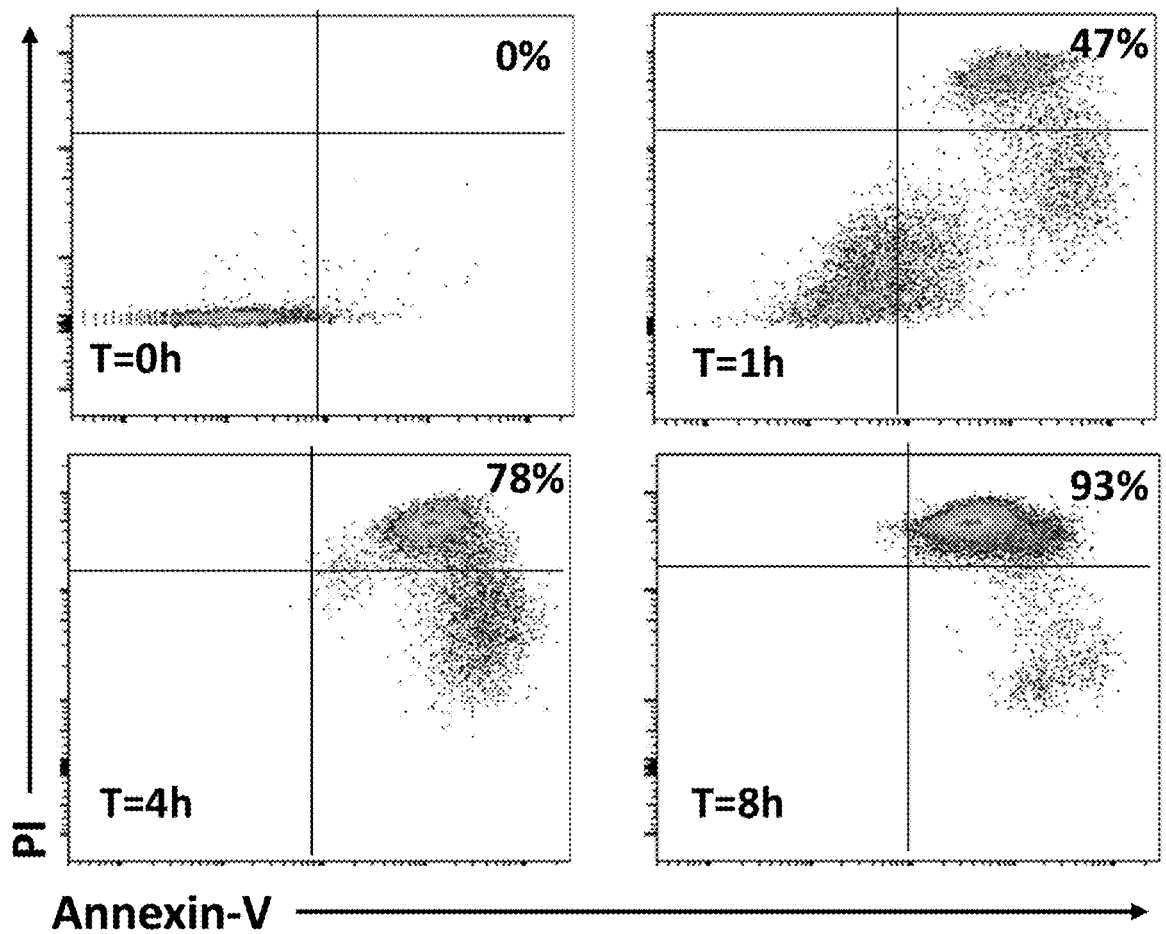
FIGS. 2A to 2C show that CA-SV40-mediated cytotoxicity of cancer cells by apoptosis is associated with induction of in situ reactive oxygen species (ROS).
Figure 2B:
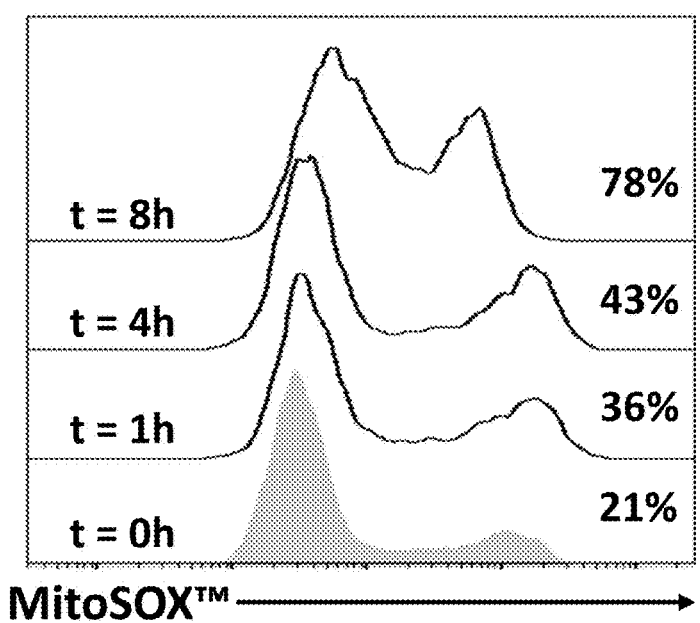
Figure 2C:
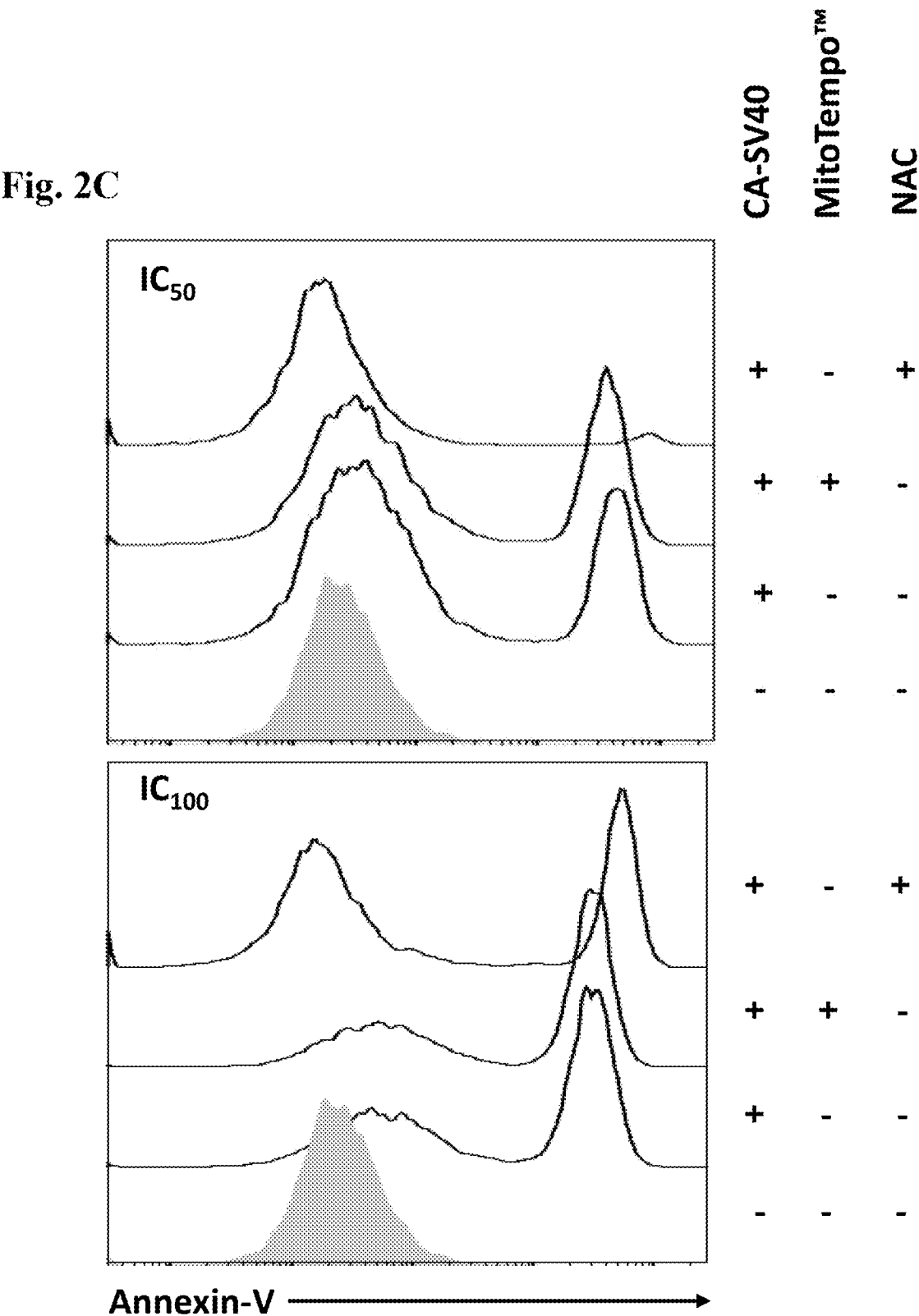

To further uncover the mechanism of cell death, we next investigated whether CA-SV40-triggered apoptosis is strictly occurring in the absence of necrosis. To do so, a co-staining experiment was conducted using propidium iodine (PI) and Annexin-V at different time points. As shown in FIG. 2A, apoptosis started occurring as of 1 h post-CA-SV40 treatment with complete death obtained after 8 h. Nevertheless, no necrotic cells (PI+/Annexin V−) were detected during this staining strategy suggesting absence of membrane damages (necrosis). Since a large number of anti-cancer molecules can trigger cell death via release or de novo production of reactive oxygen species (ROS), we next stained the EL4 lymphoma cells treated with CA-SV40 at the IC$_{50}$ dose with MitoSOX™. Flow cytometry analysis of MitoSOX signal shows a time-dependent ROS production with most cells staining positive 8 h post-treatment (FIG. 2B). This observation led us to test whether treatment with MitoTempo™ (blocking mitochondria-specific ROS) or N-acetylcysteine (NAC—building block for GSH) rescue from CA-SV40-triggered cell death. Interestingly, only NAC completely blocked apoptosis when the IC$_{50}$ dose was used with an incomplete but significant blockade observed at higher doses (IC$_{100}$—FIG. 2C).

These data demonstrate that a bile acid-NLS conjugate, CA-SV40, has a potent cytotoxic ability towards various cancer cell lines, which may be mediated through release of intracellular ROS and apoptosis.

Example 3

CA-SV40 Promotes Cargo Release in the Cytoplasm of Target Cells

Figure 3A:
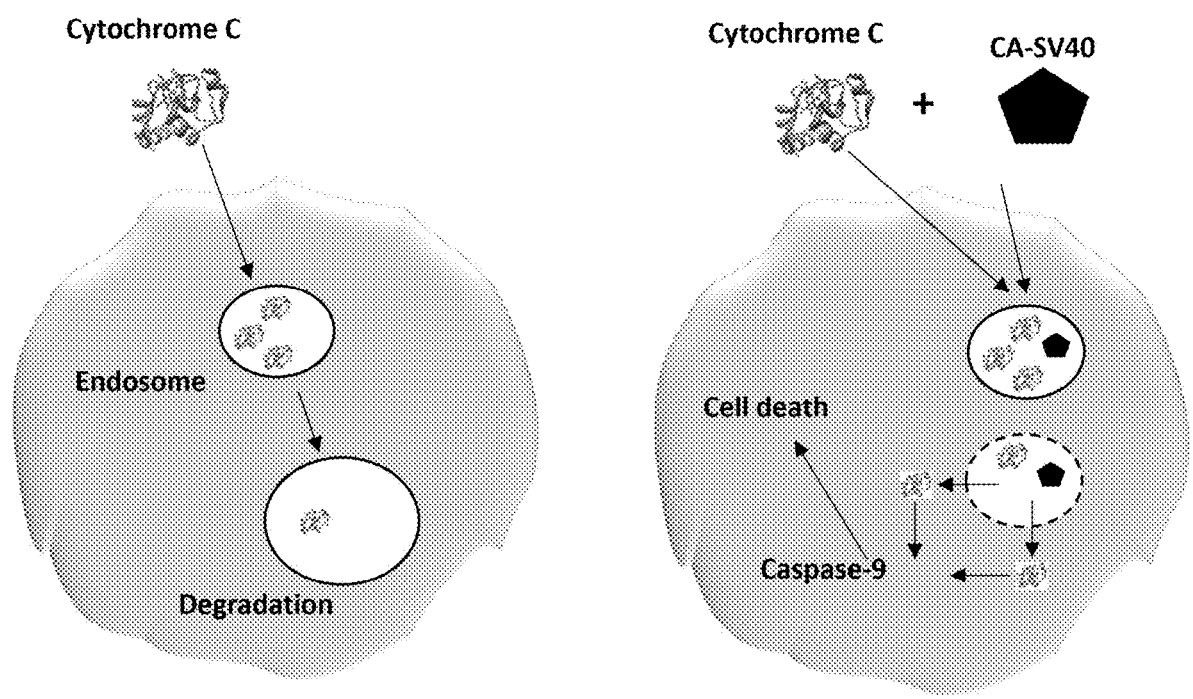
FIGS. 3A and 3B show the ability of CA-SV40 to promote cargo release in the cytoplasm of target cells.
Figure 3B:
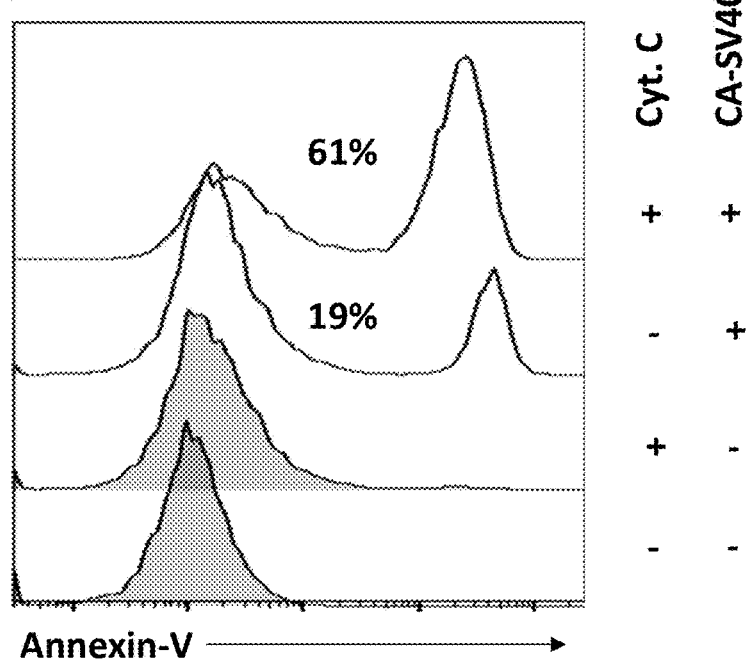

Cytochrome C is a protein that is normally entrapped in the mitochondria but can be released upon intrinsic signaling known to trigger apoptosis. An experiment was designed where recombinant cytochrome C was added to EL4 cells either alone or in combination with CA-SV40 (47 µM) (FIG. 3A). Interestingly, addition of cytochrome C alone did not trigger cell death, whereas its combination with a weak CA-SV40 dose increased cell death by three-fold (19% to 61%—FIG. 3B). These data clearly suggest that a bile acid-NLS conjugate, CA-SV40, disrupts endosomal membranes, which not only leads to cargo release, but may also perturb the entire vesicular transport system. In addition, it may explain the increase in intracellular ROS levels as it can damage endosomes/vesicles responsible for intracellular ROS transport.

Example 4

CA-SV40 Delays Tumor Growth In Vivo

Figure 4A:
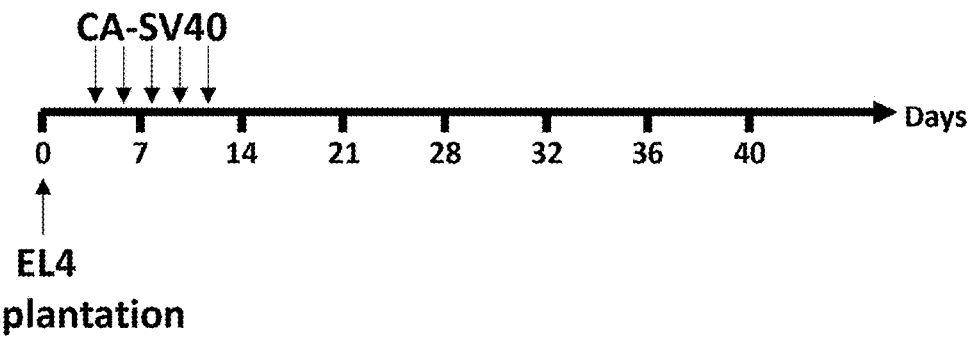
FIGS. 4A to 4F show the antitumoral effect of CA-SV40 on EL4 lymphoma in vivo.
Figure 4B:
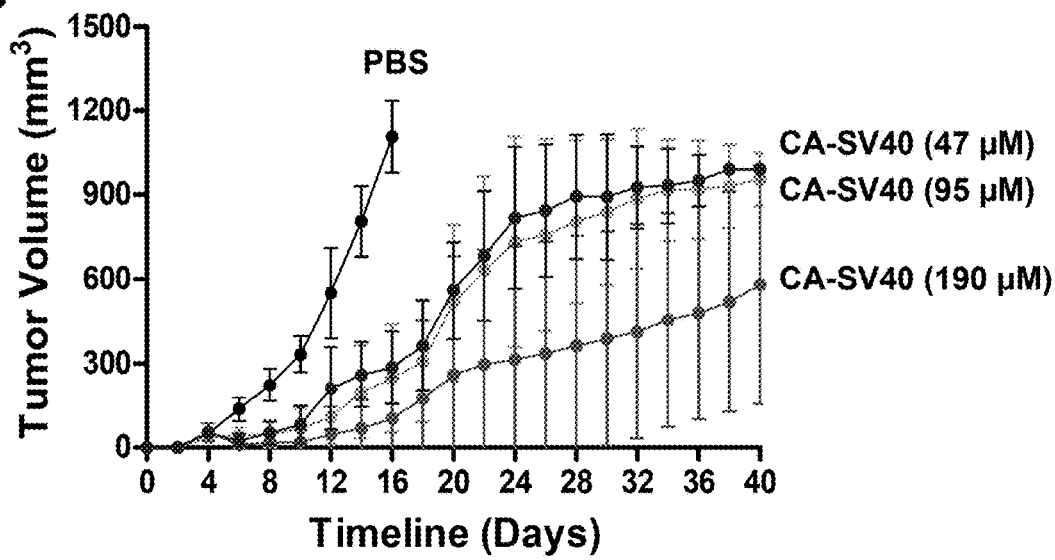
Figure 4C:
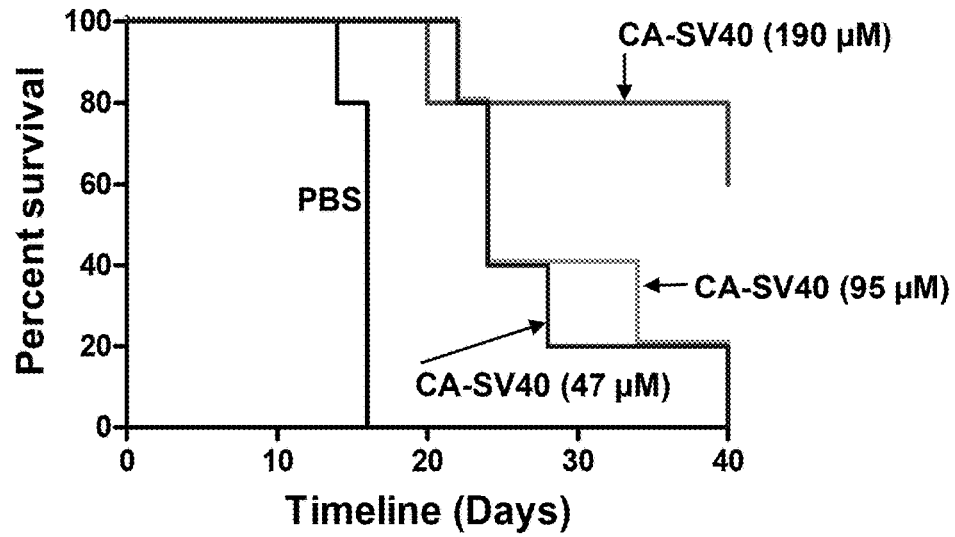
Figure 4D:
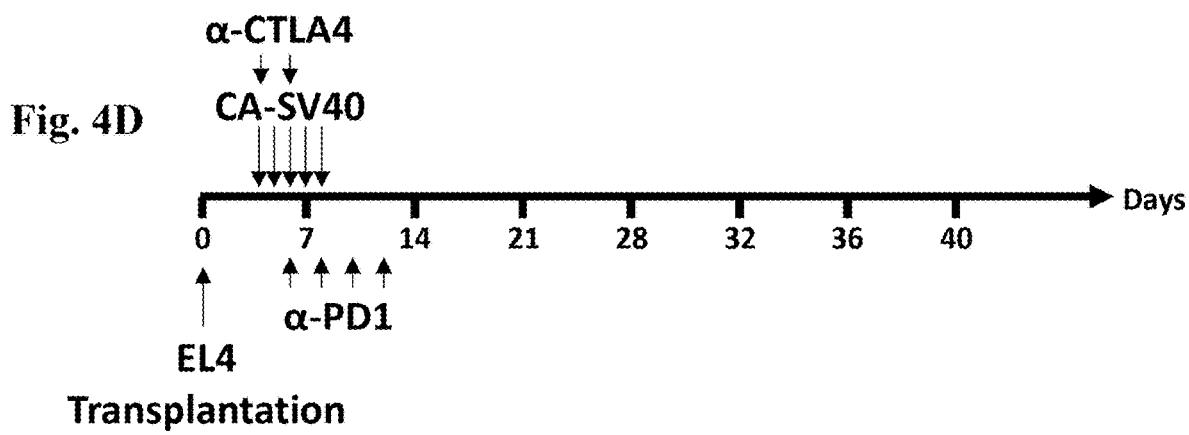
Figure 4E:
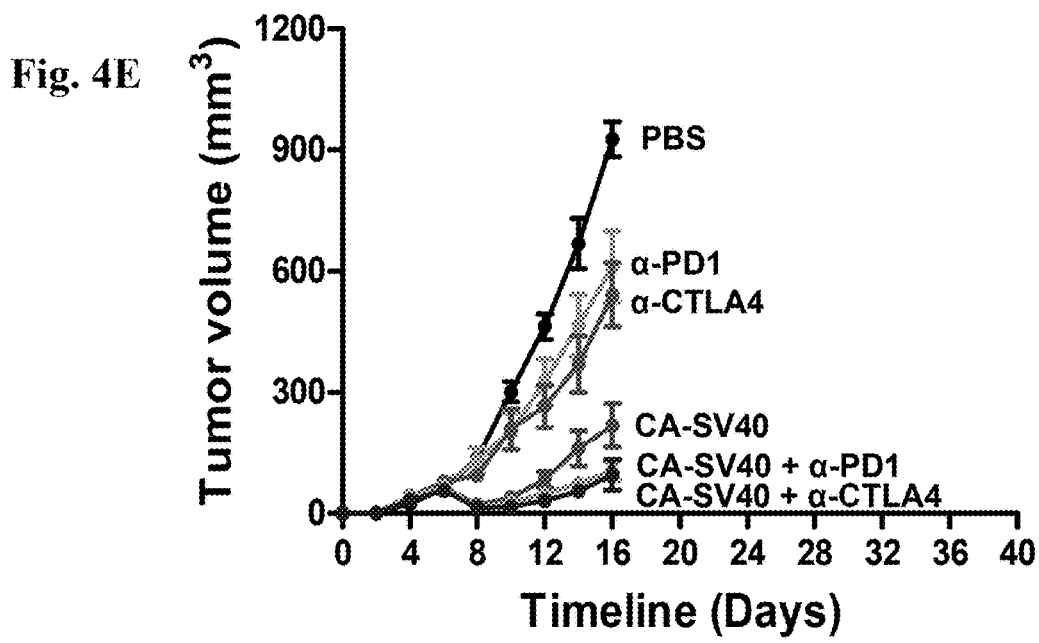
Figure 4F:
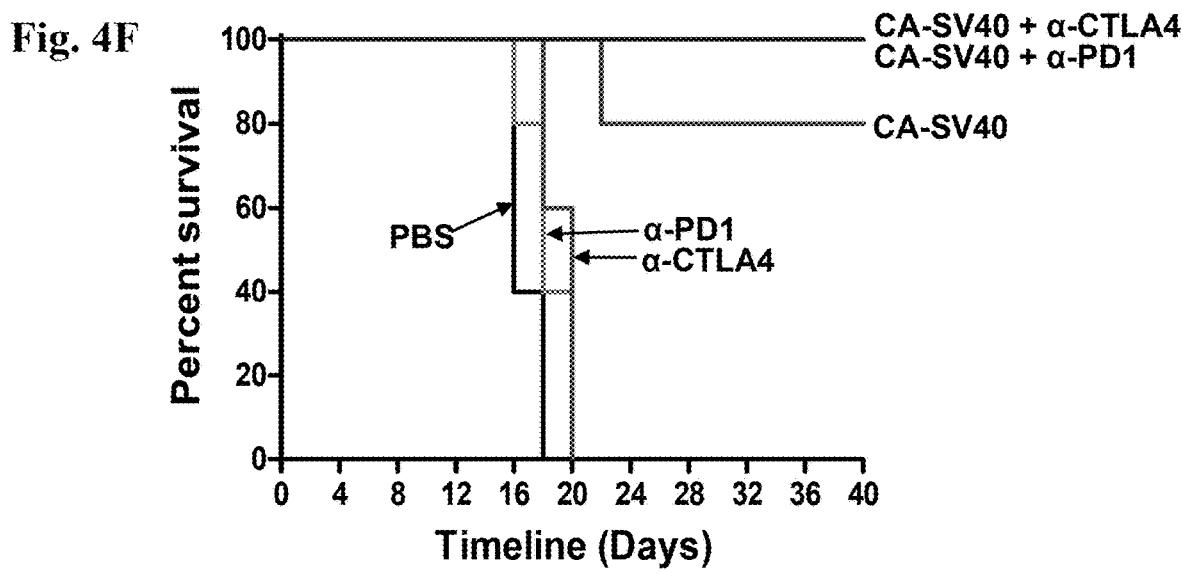

The apoptosis observations obtained in vitro prompted us to explore whether CA-SV40 administration to mice with pre-established tumors can trigger a therapeutic effect. First, CA-SV40 was delivered alone using three different doses (47 µM, 95 µM, and 190 µM) every 48 h following the appearance of palpable tumors (EL4) (FIG. 4A) for a total of 5 injections. As shown in FIG. 4B, the highest tested dose significantly delayed tumor growth resulting in a 60% survival at day 40 (FIG. 4C). To further improve this response, we next combined the highest tested CA-SV40 dose (delivered daily instead of every 48 h) with the immune-checkpoint inhibitors (ICIs) anti-PD-1 or anti-CTLA4 (FIG. 4D). Although animals treated with CA-SV40 alone exhibited significant delays in tumor growth, combining CA-SV40 with ICIs significantly enhanced the antitumoral response (FIG. 4E and FIG. 4F).

Example 5

Engineering Potent Bile Acid-NLS Conjugates with Enhanced Cytotoxic and Anti-Tumoral Properties The data obtained so far clearly demonstrate the potential of using CA-SV40 as a cytotoxic or an anti-cancer molecule. In an attempt to further enhance the pro-apoptotic potency of CA-SV40, a series of different bile acid-NLS conjugates were engineered and tested for their cytotoxic ability (FIG. 5 and FIG. 6).

Figure 5:
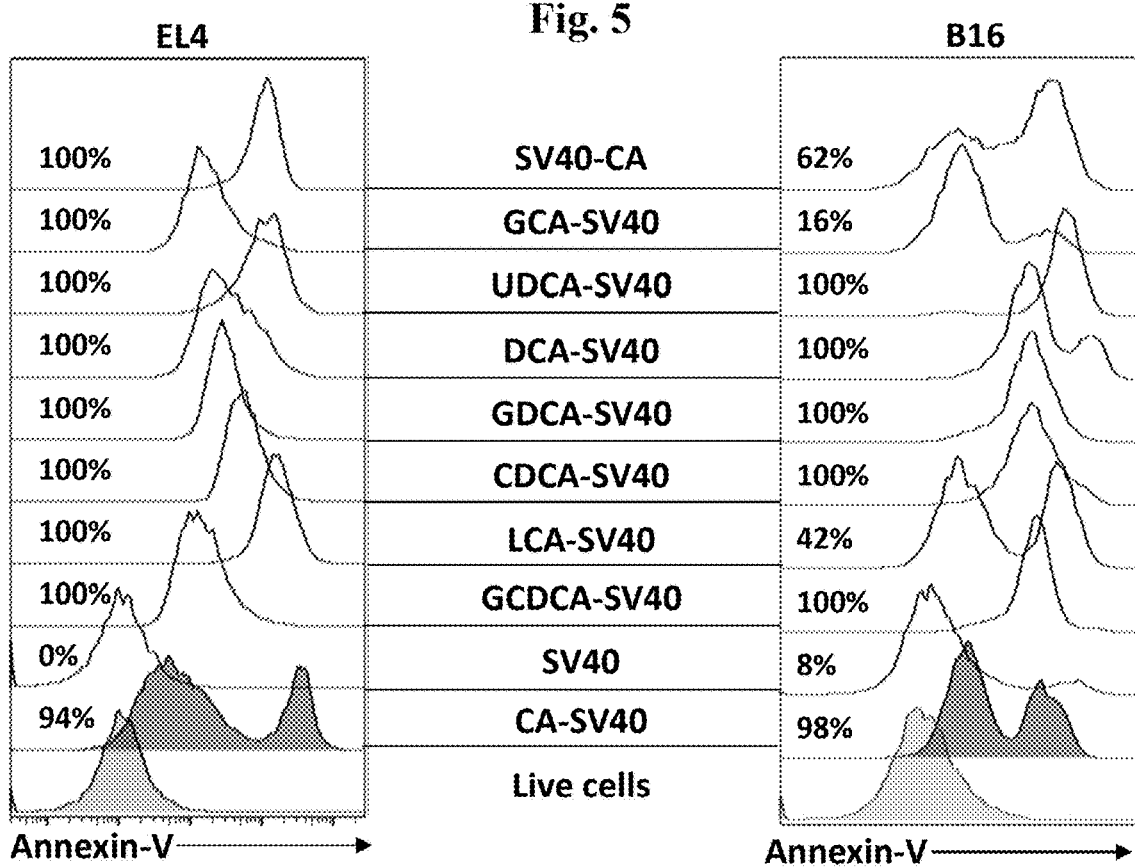
FIG. 5 shows the cytotoxic effect of different bile acid-SV40 conjugates on different cancer cell lines. Annexin-V staining percentage after treatment with different bile acid-SV40 conjugates (190 µM) is shown relative to live cancer cells (i.e., PBS treated cancer cells) by flow cytometry. Cancer cell lines tested were EL4 lymphoma, B16 melanoma, E0771 breast cancer, CT-26 colon carcinoma, 4T1 breast cancer, MBA-MD-468 triple-negative breast cancer, human H460 lung cancer, and human A549 lung cancer. Bile acids conjugated to SV40 NLS were: N-term cholic acid (CA) (i.e., CA-SV40); C-term cholic acid (CA) (i.e., SV40-CA); glycodeoxycholic acid (GDCA); glycochenodeoxycholic acid (GCDCA); chenodeoxycholic acid (CDCA); ursodeoxycholic acid (UDCA); deoxycholic acid (DCA); glycocholic acid (GCA); and lithocholic acid (LCA). SV40 alone was also tested as a negative control.
Figure 5:
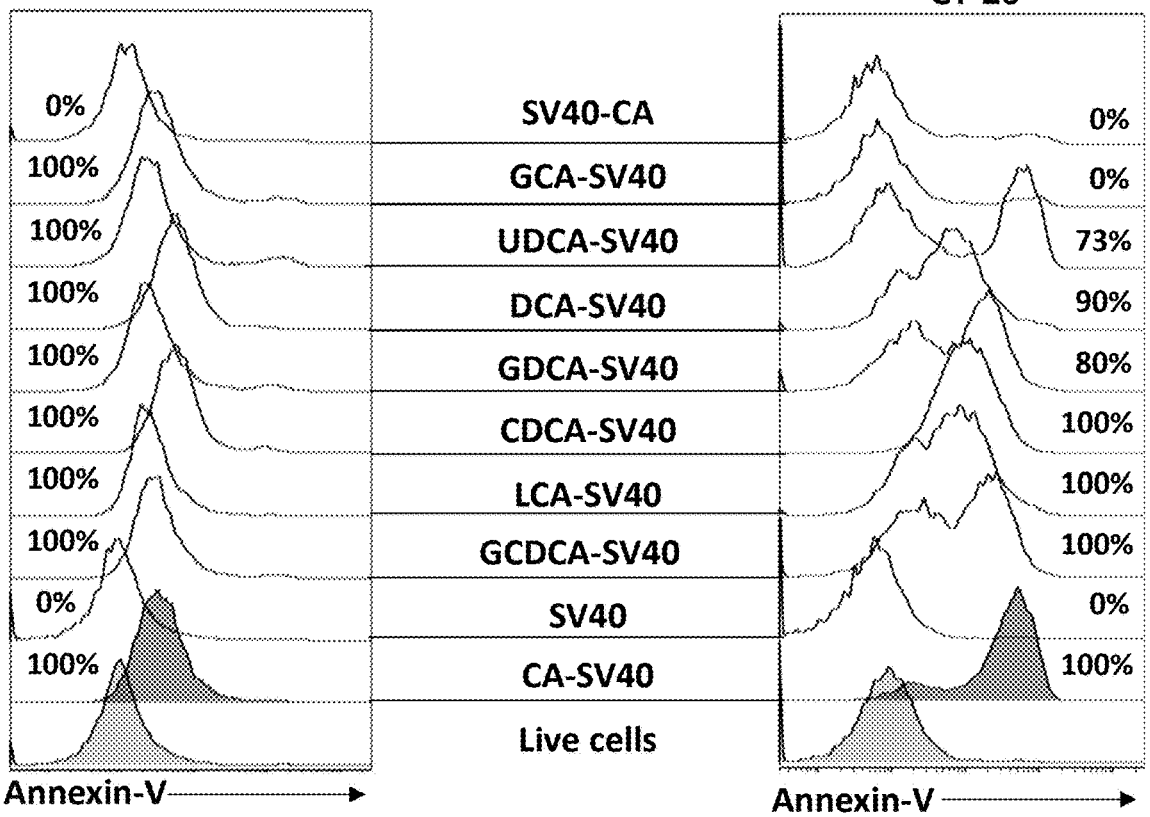
Figure 5:
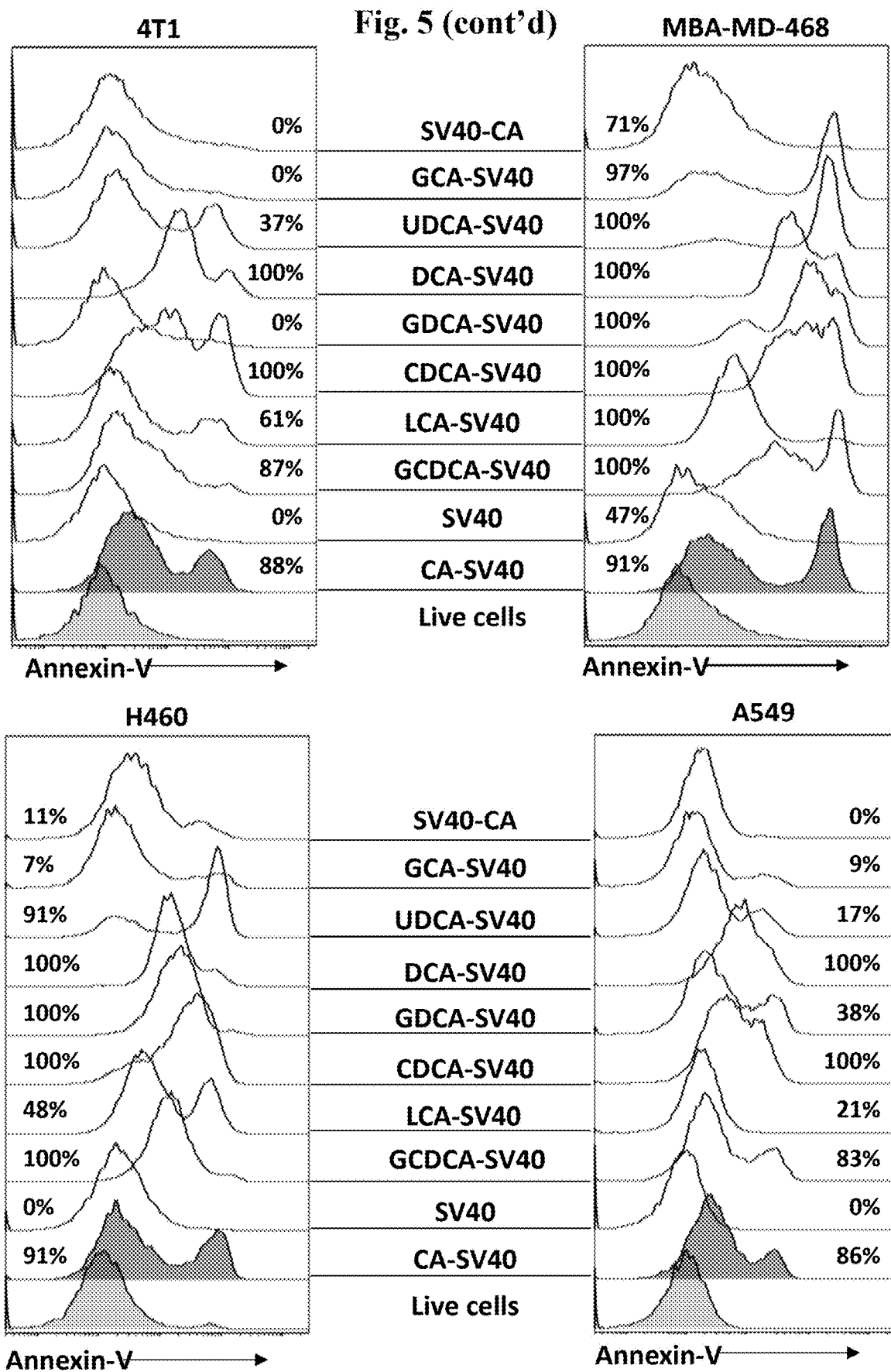

First, different bile acid-SV40 NLS conjugates were produced by changing the bile acid moiety of CA-SV40 (FIG. 5). Enhanced cell death was observed with various bile acid-SV40 conjugates when tested on EL4 lymphoma, B16 melanoma, E0771 breast cancer, CT-26 colon cancer, 4T1 breast cancer, MBA-MD-468 breast cancer, H460 lung cancer, as well as A549 lung cancer cells. Furthermore, in some cases, CA conjugated C-terminus (SV40-CA) of SV40 NLS exhibited similar cytotoxic ability in comparison to N-terminus conjugated CA (CA-SV40).

Figure 6:
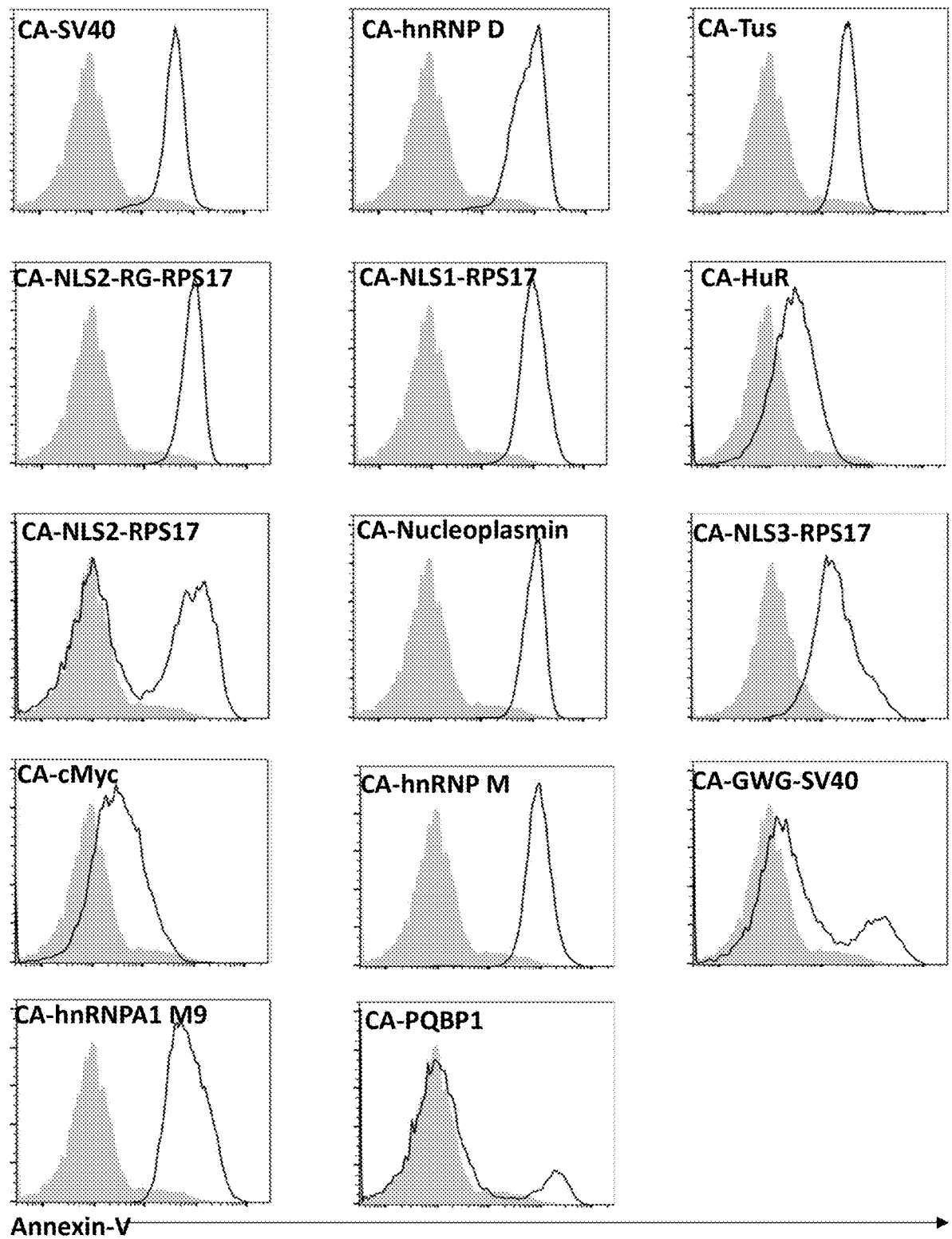
FIG. 6 shows the cytotoxic effect of different Cholic acid-NLS conjugates on cancer cells. Annexin-V staining percentage after treatment with different Cholic acid-NLS conjugates (190 µM) is shown relative to live EL4 lymphoma cells (i.e., PBS treated cancer cells) by flow cytometry. NLSs conjugated to cholic acid (CA) were: SV40 NLS; hnRNP D NLS; Tus NLS; NLS2-RG-RPS17 NLS; NLS1-RPS17; HuR; NLS2-RPS17; Nucleoplasmin; NLS3-RPS17; cMyc; hnRNP M NLS; GWG-SV40 NLS; hnRNPA1 M9 NLS; and PQBP-1 NLS.

Second, a similar engineering approach was conducted by testing other NLSs in combination with cholic acid (FIG. 6). The majority of CA-NLS conjugates tested exhibited cytotoxic activity. The cytotoxicity of CA-SV40 was notably higher than that of CA-GWG-SV40, with the only difference between the structures of the two molecules being the insertion of a GWG motif in the latter, which has been reported to facilitate endosome escape via possible insertion/retention in the endosomal membrane.

These data demonstrate the potent cytotoxic and anti-cancer activity of various bile acid-NLS conjugates, and their potential use as therapeutics.

Example 6

Different Bile Acid-NLS Conjugates Delays Tumor Growth In Vivo

Figure 7A:
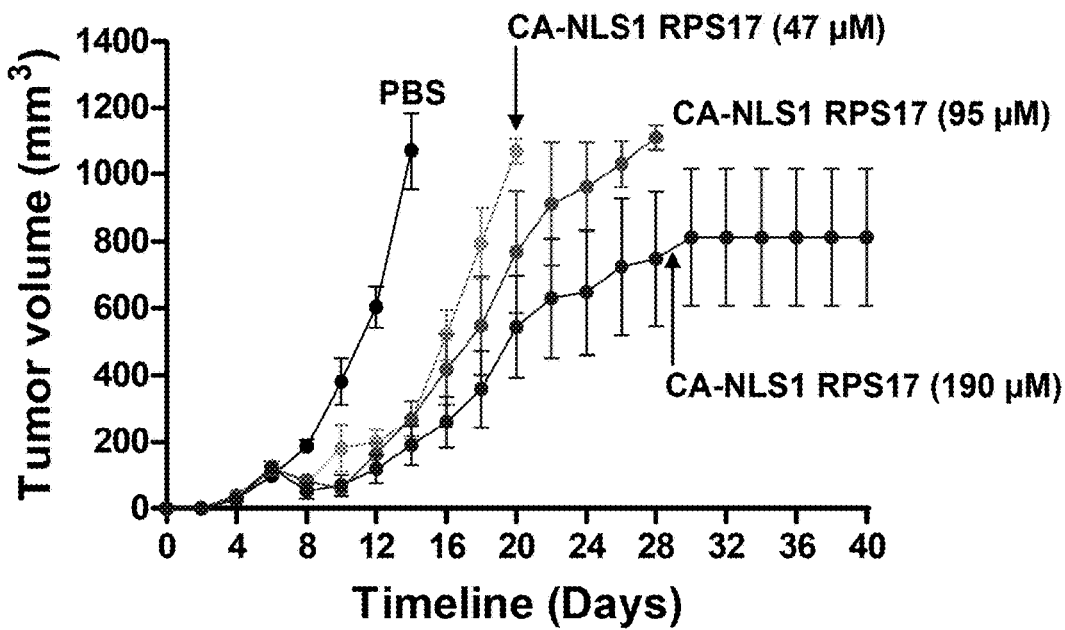
FIGS. 7A and 7B show the antitumoral effect of CA-NLS1 RPS17 on EL4 lymphoma in vivo.
Figure 7B:
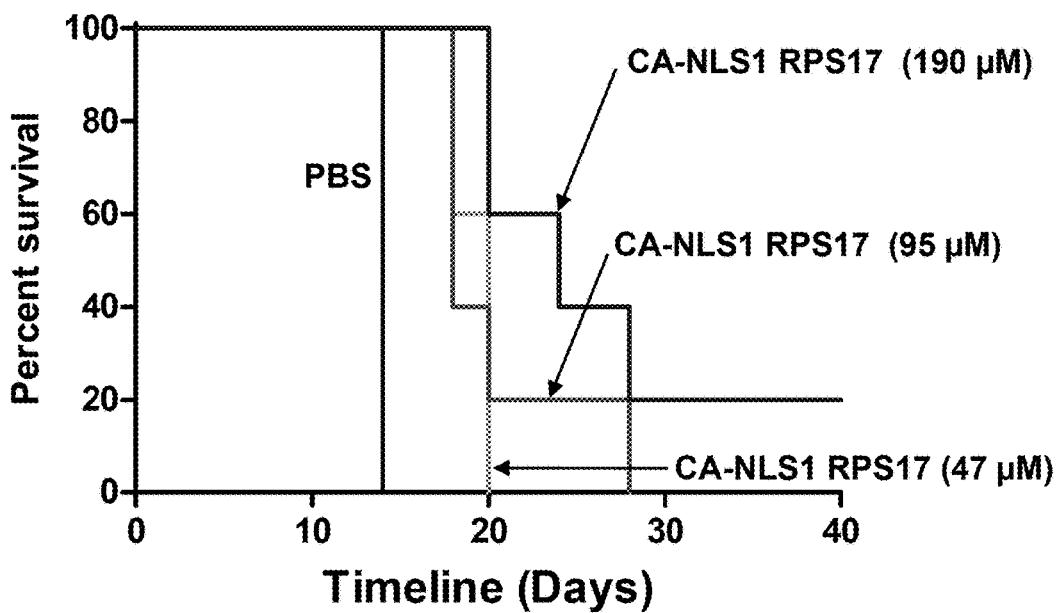
Figure 8A:
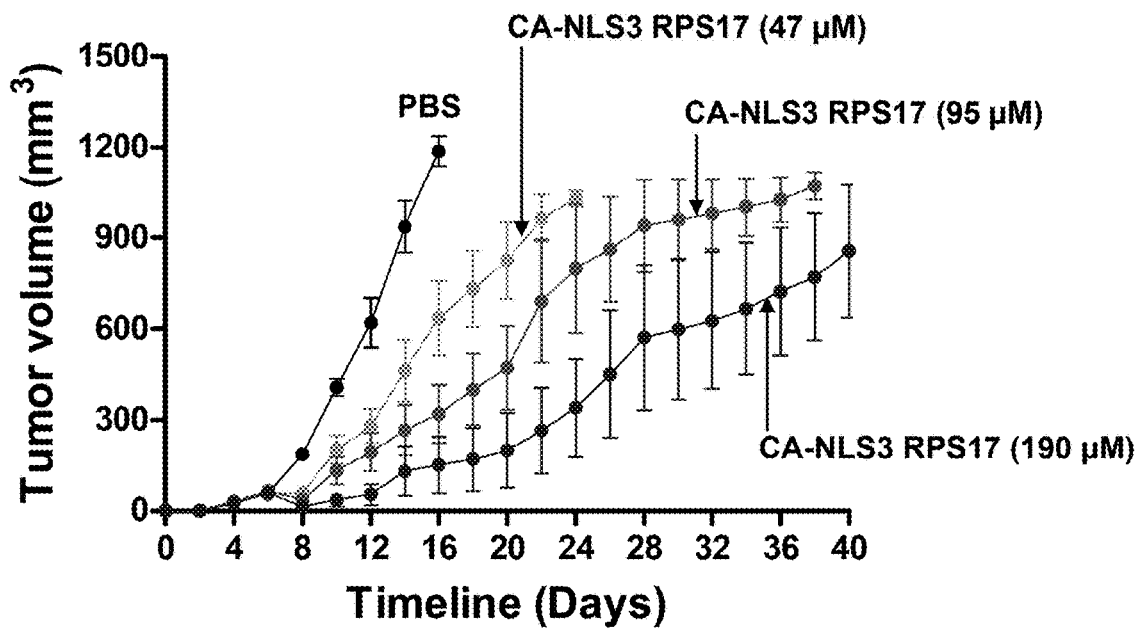
FIGS. 8A and 8B show the antitumoral effect of CA-NLS3 RPS17 on EL4 lymphoma in vivo.
Figure 8B:
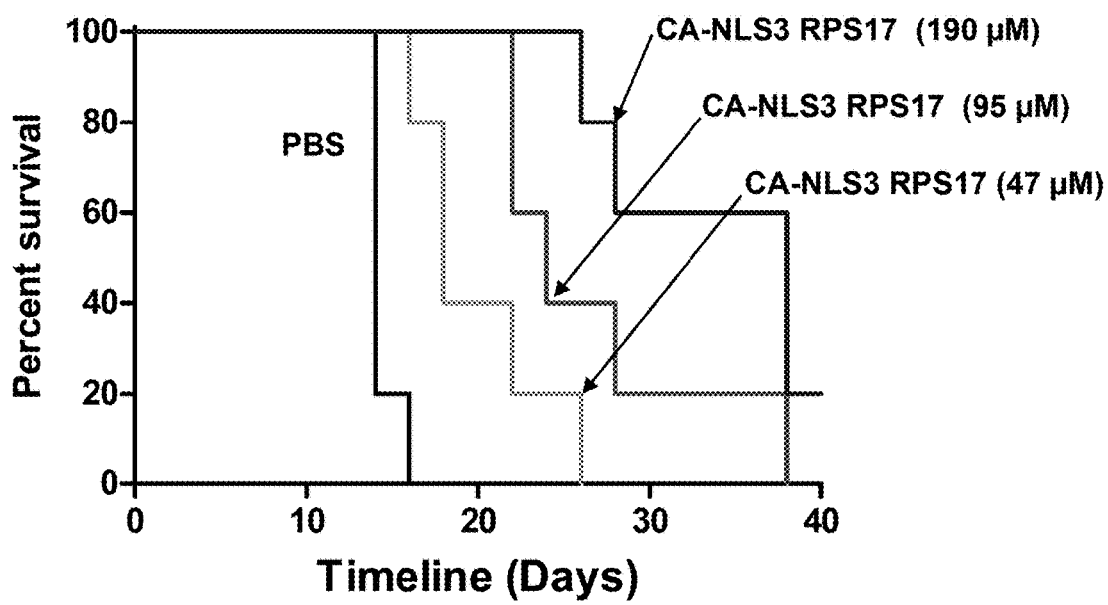

CA-NLS1 RPS17 (FIG. 7) and CA-NLS3 RPS17 (FIG. 8) were delivered alone using three different doses (47 µM, 95 µM, and 190 µM) every 48 h following the appearance of palpable tumors (EL4) for a total of 5 injections. As shown in FIGS. 7A and 8A, the highest tested dose significantly delayed tumor growth resulting in a 20% survival at day 40 (FIGS. 7B and 8B).

These data demonstrate that different bile acid-NLS conjugates have cytotoxic and anticancer activities in vivo.

REFERENCES

Beaudoin et al., (2016). ChAcNLS, a novel modification to antibody-conjugates permitting target cell-specific endosomal escape, localization to the nucleus and enhanced total intracellular accumulation. *Molecular Pharmaceutics,* 13(6): 1915-26.

Beck et al., (2017). Strategies and challenges for the next generation of antibody-drug conjugates. *Nature Reviews Drug Discovery,* 16: 315-337.

Hanafi et al., (2018). Overview of Bile Acids Signaling and Perspective on the Signal of Ursodeoxycholic Acid, the Most Hydrophilic Bile Acid, in the Heart. *Biomolecules,* 8(4): 159.

Murakami et al., (2020). Bile acids and ceramide overcome the entry restriction for GII.3 human norovirus replication in human intestinal enteroids. *Proceedings of the National Academy of Sciences USA.* 117(3):1700-1710.

Shivanna et al., (2014) The crucial role of bile acids in the entry of porcine enteric calicivirus. *Virology* 456-457, 268-278.

Shivanna et al., (2015). Ceramide formation mediated by acid sphingomyelinase facilitates endosomal escape of caliciviruses. *Virology,* 483, 218-228.

Sun et al., (2016). Factors influencing the nuclear targeting ability of nuclear localization signals. *Journal of Drug Targeting,* 24(10): 927-933.

The invention claimed is:

1. A pharmaceutical composition comprising a bile acid-peptide conjugate as a cytotoxic or cytostatic agent, the conjugate being free or releasably bound to a carrier molecule and being present in the pharmaceutical composition at an effective concentration of at least 40 micromolar, wherein the peptide comprised in the bile acid-peptide conjugate comprises a nuclear localization signal (NLS), wherein the bile acid-peptide conjugate when releasably bound to the carrier molecule is bound via an enzymatically cleavable linker, a photocleavable linker, a redox-sensitive linker, or a pH-sensitive linker, and wherein the carrier molecule is not a polypeptide antigen.

2. The pharmaceutical composition of claim 1, wherein the effective concentration of the bile acid-peptide conjugate in the pharmaceutical composition is at least 60 micromolar.

3. The pharmaceutical composition of claim 1, wherein the effective concentration of the bile acid-peptide conjugate in the pharmaceutical composition is at least 80 micromolar.

4. The pharmaceutical composition of claim 1, wherein the effective concentration of the bile acid-peptide conjugate in the pharmaceutical composition is at least 100 micromolar.

5. The pharmaceutical composition of claim 1, wherein the effective concentration of the bile acid-peptide conjugate in the pharmaceutical composition is at least 150 micromolar.

6. The pharmaceutical composition of claim 1, wherein the bile acid is: cholic acid (CA), chenodeoxycholic acid (CDCA), deoxycholic acid (DCA), lithocholic acid (LCA), glycodeoxycholic acid (GDCA), glycocholic acid (GCA), taurocholic acid (TCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (THDCA), ursodeoxycholic acid (UDCA), or glycoursodeoxycholic acid (GUDCA).

7. The pharmaceutical composition of claim 1, wherein the bile acid is an analog of CA, CDCA, DCA, LCA, GDCA, GCA, TCA, GCDCA, TDCA, GLCA, TLCA, THDCA, TCDCA, UCA, THDCA, UDCA, or GUDCA, wherein the analog: induces endocytosis; triggers ceramide accumulation on the inner leaflet of endosomes; or triggers increased acid sphingomyelinase (ASM)-mediated cleavage of sphingomyelin to form ceramide.

8. The pharmaceutical composition of claim 1, wherein the nuclear localization signal is a/an: SV40 NLS (SEQ ID NO: 1 or 2), GWG-SV40 NLS (SEQ ID NO: 3), hnRNPA1 M9 NLS (SEQ ID NO: 4), hnRNP D NLS (SEQ ID NO: 5), hnRNP M NLS (SEQ ID NO: 6), PQBP-1 NLS (SEQ ID NO: 7), NLS2-RG Domain RPS17 (SEQ ID NO: 8), NL S1 RPS17 SEQ ID NO: 9), NLS2 RPS17 (SEQ ID NO: 10), NLS3 RPS17 (SEQ ID NO: 11), cMyc NLS (SEQ ID NO: 12), HuR NLS (SEQ ID NO: 13), Tus NLS (SEQ ID NO: 14), or Nucleoplasmin NLS (SEQ ID NO: 15).

9. The pharmaceutical composition of claim 1, wherein the nuclear localization signal is a variant of an NLS having nuclear localization activity, the NLS comprising or consisting of the amino acid sequence of any one of SEQ ID NOs: 1 to 15.

10. The pharmaceutical composition of claim 1, wherein the bile acid-peptide conjugate does not comprise CA-SV40.

11. The pharmaceutical composition of claim 1 comprising the bile acid-peptide conjugate releasably bound to the carrier molecule, wherein the carrier molecule is a targeting molecule that binds to a specific target, and wherein the bile acid-peptide conjugate is released from the targeting molecule upon, or subsequent to, binding of the targeting molecule to its target.

12. The pharmaceutical composition of claim 1 comprising the bile acid-peptide conjugate releasably bound to the carrier molecule, wherein carrier molecule is: a protein carrier; a polysaccharide carrier; a polynucleotide carrier; a polynucleotide analog carrier; a polyethylene glycol carrier; or a lipid carrier.

13. The pharmaceutical composition of claim 1 comprising the bile acid-peptide conjugate releasably bound to the carrier molecule, wherein the carrier molecule is an antibody or a receptor ligand.

14. The pharmaceutical composition of claim 13, wherein the bile acid-peptide conjugate is the only cytotoxic or cytostatic agent releasably bound to the carrier molecule.

15. The pharmaceutical composition of claim 13, wherein the bile acid-peptide conjugate is the only cytotoxic or cytostatic agent comprised in the pharmaceutical composition.

16. A pharmaceutical composition comprising a bile acid-peptide conjugate as a cytotoxic or cytostatic agent, the conjugate being free or releasably bound to a carrier molecule and being present in the pharmaceutical composition at an effective concentration of at least 40 micromolar, wherein the bile acid comprises chenodeoxycholic acid (CDCA) and the peptide comprises an SV40 NLS (SEQ ID NO: 1 or 2), wherein the bile acid-peptide conjugate when releasably bound to the carrier molecule is bound via an enzymatically cleavable linker, a photocleavable linker, a redox-sensitive linker, or a pH-sensitive linker, and wherein the carrier molecule is not a polypeptide antigen.

17. The pharmaceutical composition of claim 16, comprising the bile acid-peptide conjugate releasably bound to the carrier molecule, wherein the carrier molecule is a targeting molecule that binds to a specific target, and wherein the bile acid-peptide conjugate is released from the targeting molecule upon, or subsequent to, binding of the targeting molecule to its target.

18. The pharmaceutical composition of claim 16, comprising the bile acid-peptide conjugate releasably bound to the carrier molecule, wherein carrier molecule is: a protein carrier; a polysaccharide carrier; a polynucleotide carrier; a polynucleotide analog carrier; a polyethylene glycol carrier; or a lipid carrier.

19. The pharmaceutical composition of claim 16, comprising the bile acid-peptide conjugate releasably bound to the carrier molecule, wherein the carrier molecule is an antibody or a receptor ligand.

20. The pharmaceutical composition of claim 16, wherein the bile acid-peptide conjugate is the only cytotoxic or cytostatic agent releasably bound to the carrier molecule or is the only cytotoxic or cytostatic agent comprised in the pharmaceutical composition.

* * * * *

UNITED STATES PATENT AND TRADEMARK OFFICE
CERTIFICATE OF CORRECTION

PATENT NO. : 11,890,350 B2
APPLICATION NO. : 18/056110
DATED : February 6, 2024
INVENTOR(S) : Simon Beaudoin Page 1 of 1

It is certified that error appears in the above-identified patent and that said Letters Patent is hereby corrected as shown below:

In the Claims

Column 22, Claim 6, Line 43:
"acid (THDCA)," should read: --acid (TUDCA),--.

Column 22, Claim 7, Line 48:
"UCA, THDCA, UDCA," should read: --UCA, TUDCA, UDCA,--.

Signed and Sealed this
Twenty-first Day of January, 2025

Coke Morgan Stewart
*Acting Director of the United States Patent and Trademark Office*

SEQUENCE LISTING

```
Sequence total quantity: 15
SEQ ID NO: 1           moltype = AA   length = 13
FEATURE                Location/Qualifiers
MOD_RES                1
                       note = Cholic Acid (ChAc)
source                 1..13
                       mol_type = protein
```

```
                              -continued organism = synthetic construct
SEQUENCE: 1
CGYGPKKKRK VGG                                                              13

SEQ ID NO: 2            moltype = AA  length = 7
FEATURE                 Location/Qualifiers
source                  1..7
                        mol_type = protein
                        organism = synthetic construct
SEQUENCE: 2
PKKKRKV                                                                      7

SEQ ID NO: 3            moltype = AA  length = 19
FEATURE                 Location/Qualifiers
source                  1..19
                        mol_type = protein
                        organism = synthetic construct
SEQUENCE: 3
CGWWGYGPKK KRKVGGWWG                                                        19

SEQ ID NO: 4            moltype = AA  length = 20
FEATURE                 Location/Qualifiers
source                  1..20
                        mol_type = protein
                        organism = synthetic construct
SEQUENCE: 4
CSNFGPMKGG NFGGRSSGPY                                                       20

SEQ ID NO: 5            moltype = AA  length = 20
FEATURE                 Location/Qualifiers
source                  1..20
                        mol_type = protein
                        organism = synthetic construct
SEQUENCE: 5
CSGYGKVSRR GGHQNSYKPY                                                       20

SEQ ID NO: 6            moltype = AA  length = 20
FEATURE                 Location/Qualifiers
source                  1..20
                        mol_type = protein
                        organism = synthetic construct
SEQUENCE: 6
CNEKRKEKNI KRGGNRFEPY                                                       20

SEQ ID NO: 7            moltype = AA  length = 21
FEATURE                 Location/Qualifiers
source                  1..21
                        mol_type = protein
                        organism = synthetic construct
SEQUENCE: 7
CADREEGKER RHHRREELAP Y                                                     21

SEQ ID NO: 8            moltype = AA  length = 34
FEATURE                 Location/Qualifiers
source                  1..34
                        mol_type = protein
                        organism = synthetic construct
SEQUENCE: 8
CNKRVCEEIA IIPSKKLRNK GSGRIQRGPV RGIS                                       34

SEQ ID NO: 9            moltype = AA  length = 16
FEATURE                 Location/Qualifiers
source                  1..16
                        mol_type = protein
                        organism = synthetic construct
SEQUENCE: 9
CMGRVRTKTV KKAAGG                                                           16

SEQ ID NO: 10           moltype = AA  length = 20
FEATURE                 Location/Qualifiers
source                  1..20
                        mol_type = protein
                        organism = synthetic construct
SEQUENCE: 10
CNKRVCEEIA IIPSKKLRNK                                                       20
```

```
SEQ ID NO: 11          moltype = AA  length = 20
FEATURE                Location/Qualifiers
source                 1..20
                       mol_type = protein
                       organism = synthetic construct
SEQUENCE: 11
CSKKLRNKIA GYVTHLMKRI                                                   20

SEQ ID NO: 12          moltype = AA  length = 15
FEATURE                Location/Qualifiers
source                 1..15
                       mol_type = protein
                       organism = synthetic construct
SEQUENCE: 12
CGYGPAAKRV KLDGG                                                        15

SEQ ID NO: 13          moltype = AA  length = 22
FEATURE                Location/Qualifiers
source                 1..22
                       mol_type = protein
                       organism = synthetic construct
SEQUENCE: 13
CGRFSPMGVD HMSGLSGVNV PG                                                22

SEQ ID NO: 14          moltype = AA  length = 15
FEATURE                Location/Qualifiers
source                 1..15
                       mol_type = protein
                       organism = synthetic construct
SEQUENCE: 14
CGYGKLKIKR PVKGG                                                        15

SEQ ID NO: 15          moltype = AA  length = 21
FEATURE                Location/Qualifiers
source                 1..21
                       mol_type = protein
                       organism = synthetic construct
SEQUENCE: 15
CAVKRPAATK KAGQAKKKKL D                                                 21
```